US007666438B1

(12) United States Patent
Patti et al.

(10) Patent No.: US 7,666,438 B1
(45) Date of Patent: Feb. 23, 2010

(54) MULTICOMPONENT VACCINES

(75) Inventors: Joseph M. Patti, Cumming, GA (US); Timothy J. Foster, Dublin (IE); Magnus Hook, Houston, TX (US)

(73) Assignees: Inhibitex, Inc., Alpharetta, GA (US); The Provost Fellows and Scholars of the College of the Holy and Undivived Trinity of Queen Elizabeth Near Dublin, Dublin (IE); The Texas A&M University System, College Station, TX (US)

( * ) Notice: Subject to any disclaimer, the term of this patent is extended or adjusted under 35 U.S.C. 154(b) by 297 days.

(21) Appl. No.: 10/795,267

(22) Filed: Mar. 9, 2004

Related U.S. Application Data

(62) Division of application No. 09/386,959, filed on Aug. 31, 1999, now Pat. No. 6,703,025.

(60) Provisional application No. 60/098,439, filed on Aug. 31, 1998.

(51) Int. Cl.
 *A61K 39/085* (2006.01)
(52) U.S. Cl. ............... 424/243.1; 424/192.1; 424/193.1; 424/197.11; 536/123.1
(58) Field of Classification Search ............... 424/243.1, 424/192.1, 193.1, 197.11; 536/123.1
See application file for complete search history.

(56) References Cited

U.S. PATENT DOCUMENTS 6,008,341 A * 12/1999 Foster et al. ............... 536/23.7

6,288,214 B1 * 9/2001 Hook et al. ............... 530/387.1

OTHER PUBLICATIONS

Fattom et al (Infect. Immun. Jul. 1990. 58(7): 2367-2374.*
Fattom et al (Infect. Immun. May 1996, 64(5): 1659-1665).*
Rudinger et al, in "Peptide Hormones", edited by Parsons, J.A., University Park Press, Jun. 1976, p. 6).*
Lee, "The prospects for developing a vaccine against *Staphylococcus aureus*", *Trends in Microbiology*, vol. 4, No. 4, pp. 162-166 (Apr. 1996).
Smeltzer et al "Prevalence and Chromosomal Map Location of *Staphylococcus aureus* Adhesion Genes" 1997, pp. 249-259, Gene—An International Journal on Genes and Genomes.

* cited by examiner

*Primary Examiner*—Jennifer E Graser
(74) *Attorney, Agent, or Firm*—B. Aaron Schulman; Terry L. Wright; Stites & Harbison PLLC

(57) ABSTRACT

Multicomponent vaccines are provided which aid in the prevention and treatment of staphylococcal infections and which include certain selected combinations of bacterial binding proteins or fragments thereof, or antibodies to those proteins or fragments. By careful selection of the proteins, fragments, or antibodies, a vaccine is provided that imparts protection against a broad spectrum of *Staphylococcus* and other bacterial strains and against proteins that are expressed at different stages of the logarithmic growth curve. In one embodiment of the invention, a composition is provided that includes a fibrinogen binding domain of a fibrinogen binding protein and a bacterial component such as ca capsular polysaccharide, and both active and passive vaccines based on these components are also provided, along with methods of treating infection using these compositions and vaccines.

3 Claims, 12 Drawing Sheets

CODING SEQUNCE FOR SdrF - INCLUDES FLANKING SEQUENCES

```
tattggataaattatgcttataaagtatttacataaaaatgtaaatgcaatttacaagta
 Y  W  I  N  Y  A  Y  K  V  F  T  -  K  C  K  C  N  L  Q  V
aatattcaaattatttccttgtaaatatttattttaactggaggtatagtatgaaaaag
 N  I  Q  I  I  S  L  -  N  I  Y  F  N  W  R  Y  S  M  K  K
agaagacaaggaccaattaacaagagagtggattttctatccaacaaggtaaacaagtac
 R  R  Q  G  P  I  N  K  R  V  D  F  L  S  N  K  V  N  K  Y
tcgattaggaagttcacagtaggtacagcttcaatactcgtgggtgctacgttaatgttt
 S  I  R  K  F  T  V  G  T  A  S  I  L  V  G  A  T  L  M  F
ggtgccgcagacaatgaggctaaagcggctgaagacaatcaattagaatcagcttcaaaa
 G  A  A  D  N  E  A  K  A  A  E  D  N  Q  L  E  S  A  S  K
gaagaacagaaaggtagtcgtgataatgaaaactcaaaacttaatcaagtcgatttagac
 E  E  Q  K  G  S  R  D  N  E  N  S  K  L  N  Q  V  D  L  D
aacggatcacatagttctgagaaaacaacaaatgtaaacaatgcaactgaagtaaaaaaa
 N  G  S  H  S  S  E  K  T  T  N  V  N  N  A  T  E  V  K  K
gttgaagcaccaacgacaagtgacgtatctaagcctaaagctaatgaagcagtagtgacg
 V  E  A  P  T  T  S  D  V  S  K  P  K  A  N  E  A  V  V  T
aatgagtcaactaaaccaaaaacaacagaagcaccaactgttaatgaggaatcaatagct
 N  E  S  T  K  P  K  T  T  E  A  P  T  V  N  E  E  S  I  A
gaaacacccaaaacctcaactacacaacaagattcgactgagaagaataatccatcttta
 E  T  P  K  T  S  T  T  Q  Q  D  S  T  E  K  N  N  P  S  L
aaagataatttaaattcatcctcaacgacatctaaagaaagtaaaacagacgaacattct
 K  D  N  L  N  S  S  S  T  T  S  K  E  S  K  T  D  E  H  S
actaagcaagctcaaatgtctactaataaatcaaatttagacacaaatgactctccaact
 T  K  Q  A  Q  M  S  T  N  K  S  N  L  D  T  N  D  S  P  T
caaagtgagaaaacttcatcacaagcaaataacgacagtacagataatcagtcagcacct
 Q  S  E  K  T  S  S  Q  A  N  N  D  S  T  D  N  Q  S  A  P
tctaaacaattagattcaaaaccatcagaacaaaaagtatataaaacaaaatttaatgat
 S  K  Q  L  D  S  K  P  S  E  Q  K  V  Y  K  T  K  F  N  D
gaacctactcaagatgttgaacacacgacaactaaattaaaaacaccttctgtttcaaca
 E  P  T  Q  D  V  E  H  T  T  T  K  L  K  T  P  S  V  S  T
gatagttcagtcaatgataagcaagattacacacgaagtgctgtagctagtttaggtgtt
 D  S  S  V  N  D  K  Q  D  Y  T  R  S  A  V  A  S  L  G  V
gattctaatgaaacagaagcaattacaaatgcagttagagacaatttagatttaaaagct
 D  S  N  E  T  E  A  I  T  N  A  V  R  D  N  L  D  L  K  A
gcatctagagaacaaatcaatgaagcaatcattgctgaagcactaaaaaaagacttttct
 A  S  R  E  Q  I  N  E  A  I  I  A  E  A  L  K  K  D  F  S
```

*FIG. 3*

```
aaccctgattatggtgtcgatacgccattagctctaaacagatctcaatcaaaaaattca
 N  P  D  Y  G  V  D  T  P  L  A  L  N  R  S  Q  S  K  N  S
ccacataagagtgcaagtccacgcatgaatttaatgagtttagctgctgagcctaatagt
 P  H  K  S  A  S  P  R  M  N  L  M  S  L  A  A  E  P  N  S
ggtaaaaatgtgaatgataaagttaaaatcacaaaccctacgctttcacttaataagagt
 G  K  N  V  N  D  K  V  K  I  T  N  P  T  L  S  L  N  K  S
aataatcacgctaataacgtaatatggccaacaagtaacgaacaatttaatttaaaagca
 N  N  H  A  N  N  V  I  W  P  T  S  N  E  Q  F  N  L  K  A
aattatgaattagatgacagcataaaagagggagatacttttactattaagtatggtcag
 N  Y  E  L  D  D  S  I  K  E  G  D  T  F  T  I  K  Y  G  Q
tatattagaccgggtggtttagaacttcctgcaataaaaactcaactacgtagtaaggat
 Y  I  R  P  G  G  L  E  L  P  A  I  K  T  Q  L  R  S  K  D
ggctctattgtagctaatggtgtatatgataaaactacaaatacgacgacttatacattt
 G  S  I  V  A  N  G  V  Y  D  K  T  T  N  T  T  T  Y  T  F
actaactatgttgatcaatatcaaaatattacaggtagttttgatttaattgcgacgcct
 T  N  Y  V  D  Q  Y  Q  N  I  T  G  S  F  D  L  I  A  T  P
aagagggaaacagcaattaaggataatcagaattatcctatggaagtgacgattgctaac
 K  R  E  T  A  I  K  D  N  Q  N  Y  P  M  E  V  T  I  A  N
gaagtagtcaaaaaagacttcattgtggattatggtaataaaaaggacaatacaactaca
 E  V  V  K  K  D  F  I  V  D  Y  G  N  K  K  D  N  T  T  T
gcagcggtagcaaatgtggataatgtaaataataaacataacgaagttgtttatctaaac
 A  A  V  A  N  V  D  N  V  N  N  K  H  N  E  V  V  Y  L  N
caaaataaccaaaaccctaaatatgctaaatatttctcaacagtaaaaaatggtgaattt
 Q  N  N  Q  N  P  K  Y  A  K  Y  F  S  T  V  K  N  G  E  F
ataccaggtgaagtgaaagtttacgaagtgacggataccaatgcgatggtagatagcttc
 I  P  G  E  V  K  V  Y  E  V  T  D  T  N  A  M  V  D  S  F
aatcctgatttaaatagttctaatgtaaaagatgtgacaagtcaatttgcacctaaagta
 N  P  D  L  N  S  S  N  V  K  D  V  T  S  Q  F  A  P  K  V
agtgcagatggtactagagttgatatcaattttgctagaagtatggcaaatggtaaaaag
 S  A  D  G  T  R  V  D  I  N  F  A  R  S  M  A  N  G  K  K
tatattgtaactcaagcagtgagaccaacgggaactggaaatgtttataccgaatattgg
 Y  I  V  T  Q  A  V  R  P  T  G  T  G  N  V  Y  T  E  Y  W
ttaacaagagatggtactaccaatacaaatgattttaccgtggaacgaagtctacaacg
 L  T  R  D  G  T  T  N  T  N  D  F  Y  R  G  T  K  S  T  T
gtgacttatctcaatggttcttcaacagcacaggggggataatcctacatatagtctaggt
 V  T  Y  L  N  G  S  S  T  A  Q  G  D  N  P  T  Y  S  L  G
gactatgtatggttagataaaaataaaaacggtgttcaagatgatgatgagaaaggttta
 D  Y  V  W  L  D  K  N  K  N  G  V  Q  D  D  D  E  K  G  L
```

FIG. 3 (CONT'D 1)

```
gcaggtgtttatgttactcttaaagacagtaacaatagagaattacaacgtgtaactact
 A  G  V  Y  V  T  L  K  D  S  N  N  R  E  L  Q  R  V  T  T
gatcaatctggacattatcaatttgataatttacaaaatggaacgtacacagtcgagttt
 D  Q  S  G  H  Y  Q  F  D  N  L  Q  N  G  T  Y  T  V  E  F
gcgattcctgataattatacgccatctcccgcaaataattctacaaatgatgcaatagat
 A  I  P  D  N  Y  T  P  S  P  A  N  N  S  T  N  D  A  I  D
tcagatggtgaacgtgatggtacacgtaaagtagttgttgccaaaggaacaattaataat
 S  D  G  E  R  D  G  T  R  K  V  V  V  A  K  G  T  I  N  N
gctgataatatgactgtagatactggcttttatttaactcctaaatacaatgtcggagat
 A  D  N  M  T  V  D  T  G  F  Y  L  T  P  K  Y  N  V  G  D
tatgtatgggaagatacaaataaagatggtatccaagatgacaatgaaaaaggaatttct
 Y  V  W  E  D  T  N  K  D  G  I  Q  D  D  N  E  K  G  I  S
ggtgttaaagtaacgttaaaaaataaaaatggagatactattggcacaacgacaacagat
 G  V  K  V  T  L  K  N  K  N  G  D  T  I  G  T  T  T  T  D
tcaaatggtaaatatgaattcacaggtttagagaacggggattacacaatagaatttgag
 S  N  G  K  Y  E  F  T  G  L  E  N  G  D  Y  T  I  E  F  E
acgccggaaggctacacaccgactaaacaaaactcgggaagtgacgaaggtaaagattca
 T  P  E  G  Y  T  P  T  K  Q  N  S  G  S  D  E  G  K  D  S
aacggtacgaaaacaacagtcacagtcaaagatgcagataataaaacaatagactcaggt
 N  G  T  K  T  T  V  T  V  K  D  A  D  N  K  T  I  D  S  G
ttctacaagccaacatataacttaggtgactatgtatgggaagatacaaataaagatggt
 F  Y  K  P  T  Y  N  L  G  D  Y  V  W  E  D  T  N  K  D  G
attcaagacgacagtgaaaaagggatttctggggttaaagtgacgttaaaagataaaaat
 I  Q  D  D  S  E  K  G  I  S  G  V  K  V  T  L  K  D  K  N
ggaaatgccattgggacaacgacaacagacgcaagtggtcattatcaatttaaaggatta
 G  N  A  I  G  T  T  T  T  D  A  S  G  H  Y  Q  F  K  G  L
gaaaatggaagctacacagttgagtttgagacaccatcaggttatacaccgacaaaagcg
 E  N  G  S  Y  T  V  E  F  E  T  P  S  G  Y  T  P  T  K  A
aattcaggtcaagatataactgtagattccaacggtataacaacaacaggtatcattaac
 N  S  G  Q  D  I  T  V  D  S  N  G  I  T  T  T  G  I  I  N
ggagctgataatctcacaattgatagtggtttctacaaaacaccaaaatatagtgtcgga
 G  A  D  N  L  T  I  D  S  G  F  Y  K  T  P  K  Y  S  V  G
gattatgtatgggaagatacaaataaagatggtatccaagatgacaatgaaaagggaatt
 D  Y  V  W  E  D  T  N  K  D  G  I  Q  D  D  N  E  K  G  I
tctggtgttaaagtaacgttaaaggatgaaaaaggaaatataattagcactacaacaact
 S  G  V  K  V  T  L  K  D  E  K  G  N  I  I  S  T  T  T  T
gatgaaaatgggaagtatcaatttgataatttagatagtggtaattacattattcatttt
 D  E  N  G  K  Y  Q  F  D  N  L  D  S  G  N  Y  I  I  H  F
```

*FIG. 3 (CONT'D 2)*

```
gagaaaccggaaggcatgactcaaactacagcaaattctggaaatgatgatgaaaaagat
 E   K   P   E   G   M   T   Q   T   T   A   N   S   G   N   D   D   E   K   D
gctgatggggaagatgttcgtgttacgattactgatcatgatgactttagtatagataat
 A   D   G   E   D   V   R   V   T   I   T   D   H   D   D   F   S   I   D   N
ggttattttgacgatgattcagacagtgactcagacgcagatagtgattcagactcagac
 G   Y   F   D   D   D   S   D   S   D   S   D   A   D   S   D   S   D   S   D
agtgactcggacgcagacagcgattctgacgcagacagtgactcagacgcagatagtgat
 S   D   S   D   A   D   S   D   S   D   A   D   S   D   S   D   A   D   S   D
tctgactcagacagcgactcagacgcagatagtgattccgattcagacagcgactcggat
 S   D   S   D   S   D   S   D   A   D   S   D   S   D   S   D   S   D   S   D
tcagatagtgattcggatgcagacagcgactcggattctgacagtgattctgacgcagac
 S   D   S   D   A   D   S   D   S   D   S   D   S   D   S   D   S   D   A   D
agtgactcagattcagacagtgactcggattcagacagcgattcggattccgattcagac
 S   D   S   D   S   D   S   D   S   D   S   D   S   D   S   D   S   D   S   D
agtgactcggattcagacagtgactcagactccgacagtgattccgattcagatagcgac
 S   D   S   D   S   D   S   D   S   D   S   D   S   D   S   D   S   D   S   D
tccgacgcagatagtgattcggacgcagacagtgactcagattcagacagtgattcggac
 S   D   A   D   S   D   A   D   S   D   S   D   S   D   S   D   S   D   S   D
gcagacagtgactcggactcagatagtgattcagatgcagacagcgattcagactcagat
 A   D   S   D   S   D   S   D   S   D   A   D   S   D   S   D   S   D
agcgactcggattcagacagcgactccgacgcagacagcgactcggattcagatagtgat
 S   D   S   D   S   D   S   D   S   D   A   D   S   D   S   D   S   D
tctgactcagacagtgactcagattccgatagtgattcggattcagatagtgattccgac
 S   D   S   D   S   D   S   D   S   D   S   D   S   D   S   D   S   D   S   D
gcagacagcgattcggattccgatagcgattcagactcagacagcgattcagattcagac
 A   D   S   D   S   D   S   D   S   D   S   D   S   D   S   D   S   D   S   D
agcgactcagattcagatagtgattccgacgcagacagcgatgcagacagcgactcagac
 S   D   S   D   S   D   S   D   S   D   A   D   S   D   A   D   S   D   S   D
gcagacagtgattcagatgcagacagcgattctgactcagatagtgactcagacgcagat
 A   D   S   D   S   D   A   D   S   D   S   D   S   D   S   D   S   D   A   D
agtgattccgattccgatagcgattcagattctgatagtgactcagactcagacagtgac
 S   D   S   D   S   D   S   D   S   D   S   D   S   D   S   D   S   D   S   D
tcagattccgatagcgactcggattcagatagtgattccgacgcagacagtgactcagac
 S   D   S   D   S   D   S   D   S   D   S   D   S   D   S   D   S   D   S   D
tcagatagtgactcggattccgatagtgattccgacgcagacagcgattctgactcagat
 S   D   S   D   S   D   S   D   S   D   S   D   A   D   S   D   S   D   S   D
agtgactcagacgcagatagtgattccgattccgatagcgattcggatgcagacagcgac
 S   D   S   D   A   D   S   D   S   D   S   D   S   D   A   D   S   D
```

FIG. 3 (CONT'D 3)

```
tcggattcagatagtgattccgacgcagacagtgactcagactcagatagtgactcggat
 S  D  S  D  S  D  S  D  A  D  S  D  S  D  S  D  S  D  S  D
tccgatagtgattccgacgcagacagcgattcggattccgatagcgattcagactccgac
 S  D  S  D  S  D  A  D  S  D  S  D  S  D  S  D  S  D  S  D
agcgattcagattcagacagcgactcagattccgatagtgattccgattcagacagtgac
 S  D  S  D  S  D  S  D  S  D  S  D  S  D  S  D  S  D  S  D
tcggattccgatagtgactcagactcagacagtgactcagattcagatagcgactcagat
 S  D  S  D  S  D  S  D  S  D  S  D  S  D  S  D  S  D  S  D
tcagacagtgattcggactcagatagtgactccgattcagacagtgattcggattccgat
 S  D  S  D  S  D  S  D  S  D  S  D  S  D  S  D  S  D  S  D
agcgattcggattccgatagtgactcggattcagacagtgattcggactcagacagcgac
 S  D  S  D  S  D  S  D  S  D  S  D  S  D  S  D  S  D  S  D
tccgattcagatagtgattccgactcagacagcgattcggattccgatagtgactcggat
 S  D  S  D  S  D  S  D  S  D  S  D  S  D  S  D  S  D  S  D
tcagacagtgattcggactcagacagcgactccgattcagatagtgattccgacgcagac
 S  D  S  D  S  D  S  D  S  D  S  D  S  D  S  D  S  D  A  D
agcgactccgattcagatagtgattcggacgcagacagcgattccgatagtgactcggat
 S  D  S  D  S  D  S  D  S  D  A  D  S  D  S  D  S  D  S  D
tcagacagtgattcggactcagacagcgattccgattcagacagtgactcggactcagat
 S  D  S  D  S  D  S  D  S  D  S  D  S  D  S  D  S  D  S  D
agcgactcggattcagacagtgactcggactcagatagtgactccgattcagacagcgac
 S  D  S  D  S  D  S  D  S  D  S  D  S  D  S  D  S  D  S  D
tcggattctgataaaaatgcaaaagataaattacctgatacaggagcaaatgaagatcat
 S  D  S  D  K  N  A  K  D  K  L  P  D  T  G  A  N  E  D  H
gattctaaaggcacattacttggaactttatttgcaggtttaggagcattattattagga
 D  S  K  G  T  L  L  G  T  L  F  A  G  L  G  A  L  L  L  G
agacgtcgtaaaaaagataataaagaaaaatagcactattgattcattcataagttattt
 R  R  R  K  K  D  N  K  E  K  *  H  Y  -  F  I  H  K  L  F
caagccaggtctatatggcctggtttgaaatcatattaaattgaaaggagaaaaagatga
 Q  A  R  S  I  W  P  G  L  K  S  Y  -  I  E  R  R  K  R  -
gtatgg
 V  W
```

FIG. 3 (CONT'D 4)

SdrG coding and flanking sequences.

```
atattgcaaaaaagacttatatactatattgtattttactctagaaacgattttttacttgaa
   I A K K T Y I L Y C I L L - K R F L L E
aattacattgaaatagtcaaagataaggagttttttatgattaaaaaaaaataatttacta
   N Y I E I V K D K E F L -  L K K N N L L
actaaaaagaaacctatagcaaataaatccaataaatatgcaattagaaaattcacagta
   T K K K P I A N K S N K Y A I R K F T V
ggtacagcgtctattgtaataggtgcagcattattgtttggtttaggtcataatgaggcc
   G T A S I V I G A A L L F G L G H N E A
aaagctgaggagaatacagtacaagacgttaaagattcgaatatggatgatgaattatca
   K A E E N T V Q D V K D S N M D D E L S
gatagcaatgatcagtccagtaatgaagaaaagaatgatgtaatcaataatagtcagtca
   D S N D Q S S N E E K N D V I N N S Q S
ataaacaccgatgatgataaccaaataaaaaaagaagaaacgaatagcaacgatgccata
   I N T D D D N Q I K K E E T N S N D A I
gaaaatcgctctaaagatataacacagtcaacaacaaatgtagatgaaaacgaagcaaca
   E N R S K D I T Q S T T N V D E N E A T
tttttacaaaagacccctcaagataatactcagcttaaagaagaagtggtaaaagaaccc
   F L Q K T P Q D N T Q L K E E V V K E P
tcatcagtcgaatcctcaaattcatcaatggatactgcccaacaaccatctcatacaaca
   S S V E S S N S S M D T A Q Q P S H T T
ataaatagtgaagcatctattcaaacaagtgataatgaagaaaattcccgcgtatcagat
   I N S E A S I Q T S D N E E N S R V S D
tttgctaactctaaaataatagagagtaacactgaatccaataaagaagagaatactata
   F A N S K I I E S N T E S N K E E N T I
gagcaacctaacaaagtaagagaagattcaataacaagtcaaccgtctagctataaaaat
   E Q P N K V R E D S I T S Q P S S Y K N
atagatgaaaaatttcaaatcaagatgagttattaaatttaccaataaatgaatatgaa
   I D E K I S N Q D E L L N L P I N E Y E
aataaggttagaccgttatctacaacatctgcccaaccatcgagtaagcgtgtaaccgta
   N K V R P L S T T S A Q P S S K R V T V
aatcaattagcggcagaacaaggttcgaatgttaatcatttaattaaagttactgatcaa
   N Q L A A E Q G S N V N H L I K V T D Q
agtattactgaaggatatgatgatagtgatggtattattaaagcacatgatgctgaaaac
   S I T E G Y D D S D G I I K A H D A E N
ttaatctatgatgtaacttttgaagtagatgataaggtgaaatctggtgatacgatgaca
   L I Y D V T F E V D D K V K S G D T M T
```

*FIG. 4*

```
gtgaatatagataagaatacagttccatcagatttaaccgatagttttgcaataccaaaa
 V  N  I  D  K  N  T  V  P  S  D  L  T  D  S  F  A  I  P  K
ataaaagataattctggagaaatcatcgctacaggtacttatgacaacacaaataaacaa
 I  K  D  N  S  G  E  I  I  A  T  G  T  Y  D  N  T  N  K  Q
attacctacacttttacagattatgtagataaatatgaaaatattaaagcgcaccttaaa
 I  T  Y  T  F  T  D  Y  V  D  K  Y  E  N  I  K  A  H  L  K
ttaacatcatacattgataaatcaaaggttccaaataataacactaagttagatgtagaa
 L  T  S  Y  I  D  K  S  K  V  P  N  N  N  T  K  L  D  V  E
tataagacggccctttcatcagtaaataaaacaattacggttgaatatcaaaaacctaac
 Y  K  T  A  L  S  S  V  N  K  T  I  T  V  E  Y  Q  K  P  N
gaaaatcggactgctaaccttcaaagtatgttcacaaacatagatacgaaaaaccataca
 E  N  R  T  A  N  L  Q  S  M  F  T  N  I  D  T  K  N  H  T
gttgagcaaacgatttatattaaccctcttcgttattcagccaaagaaacaaatgtaaat
 V  E  Q  T  I  Y  I  N  P  L  R  Y  S  A  K  E  T  N  V  N
atttcagggaatggcgatgaaggttcaacaattatcgacgatagtacaatcattaaagtt
 I  S  G  N  G  D  E  G  S  T  I  I  D  D  S  T  I  I  K  V
tataaggttggagataatcaaaatttaccagatagtaacagaatttatgattacagtgaa
 Y  K  V  G  D  N  Q  N  L  P  D  S  N  R  I  Y  D  Y  S  E
tatgaagatgtcacaaatgatgattatgcccaattaggaaataataatgacgtgaatatt
 Y  E  D  V  T  N  D  D  Y  A  Q  L  G  N  N  N  D  V  N  I
aattttggtaatatagattcaccatatattattaaagttattagtaaatatgaccctaat
 N  F  G  N  I  D  S  P  Y  I  I  K  V  I  S  K  Y  D  P  N
aaggacgattacacgacgatacagcaaactgtgacaatgcaaacgactataaatgagtat
 K  D  D  Y  T  T  I  Q  Q  T  V  T  M  Q  T  T  I  N  E  Y
actggtgagtttagaacagcatcctatgataatacaattgctttctctacaagttcaggt
 T  G  E  F  R  T  A  S  Y  D  N  T  I  A  F  S  T  S  S  G
caaggacaaggtgacttgcctcctgaaaaaacttataaaatcggagattacgtatgggaa
 Q  G  Q  G  D  L  P  P  E  K  T  Y  K  I  G  D  Y  V  W  E
gatgtagataaagatggtattcaaaatacaaatgataatgaaaaaccgcttagtaatgta
 D  V  D  K  D  G  I  Q  N  T  N  D  N  E  K  P  L  S  N  V
ttggtaactttgacgtatcctgatggaacttcaaaatcagtcagaacagatgaagagggg
 L  V  T  L  T  Y  P  D  G  T  S  K  S  V  R  T  D  E  E  G
aaatatcaatttgatgggttaaaaaacggattgacttataaaattacattcgaaacaccg
 K  Y  Q  F  D  G  L  K  N  G  L  T  Y  K  I  T  F  E  T  P
gaaggatatacgccgacgcttaaacattcaggaacaaatcctgcactagactcagaaggc
 E  G  Y  T  P  T  L  K  H  S  G  T  N  P  A  L  D  S  E  G
aattctgtatgggtaactattaacggacaagacgatatgactattgatagcggatttat
 N  S  V  W  V  T  I  N  G  Q  D  D  M  T  I  D  S  G  F  Y
```

FIG. 4 (CONT'D 1)

```
caaacacctaaatatagcttagggaactatgtatggtatgacactaataaagatggtatt
 Q   T   P   K   Y   S   L   G   N   Y   V   W   Y   D   T   N   K   D   G   I
caaggtgatgatgaaaaggaatctctggagtaaaagtgacgttaaaagatgaaaacgga
 Q   G   D   D   E   K   G   I   S   G   V   K   V   T   L   K   D   E   N   G
aatatcattagtacaacaacaactgatgaaaatggaaagtatcaatttgataatttaaat
 N   I   I   S   T   T   T   T   D   E   N   G   K   Y   Q   F   D   N   L   N
agtggtaattatattgttcatttt gataaaccttcaggtatgactcaaacaacaacagat
 S   G   N   Y   I   V   H   F   D   K   P   S   G   M   T   Q   T   T   T   D
tctggtgatgatgacgaacaggatgctgatggggaagaagtccatgtaacaattactgat
 S   G   D   D   D   E   Q   D   A   D   G   E   E   V   H   V   T   I   T   D
catgatgactttagtatagataacggatactatgatgacgactcagattcagatagtgat
 H   D   D   F   S   I   D   N   G   Y   Y   D   D   D   S   D   S   D   S   D
tcagactcagatagcgacgactcagactccgatagcgattccgactcagacagcgactca
 S   D   S   D   S   D   D   S   D   S   D   S   D   S   D   S   D   S   D   S
gattccgatagtgattcagattcagacagtgactcagactcagatagtgattcagattca
 D   S   D   S   D   S   D   S   D   S   D   S   D   S   D   S   D   S   D   S
gacagcgattccgactcagacagtgactcaggattagacaatagctcagataagaataca
 D   S   D   S   D   S   D   S   D   S   G   L   D   N   S   S   D   K   N   T
aaagataaattaccggatacaggagctaatgaagatcatgattctaaaggcacattactt
 K   D   K   L   P   D   T   G   A   N   E   D   H   D   S   K   G   T   L   L
ggagctttatttgcaggtttaggagcgttattattagggaagcgtcgcaaaaatagaaaa
 G   A   L   F   A   G   L   G   A   L   L   L   G   K   R   R   K   N   R   K
aataaaaattaaattattcaaatgaaattagtgaaagaagcagatacgacatttgaatag
 N   K   N   *   I   I   Q   M   K   L   V   K   E   A   D   T   T   F   E   -
aaagtatatttagtccaacaaatataaggtgttg
 K   V   Y   L   V   Q   Q   I   -   G   V
```

FIG. 4 (CONT'D 2)

SdrH coding region

```
atgaaaaagtttaacattaaacattcatttatgcttacgggctttgctttcatggtaact
 M  K  K  F  N  I  K  H  S  F  M  L  T  G  F  A  F  M  V  T
acatcattattcagtcaccaagcacatgctgaaggtaatcatcctattgacattaatttt
 T  S  L  F  S  H  Q  A  H  A  E  G  N  H  P  I  D  I  N  F
tctaaagatcaaattgataaaaatacagctaagagcaatattatcaatcgagtgaatgac
 S  K  D  Q  I  D  R  N  T  A  K  S  N  I  I  N  R  V  N  D
actagtcgcacaggaattagtatgaattcggataatgatttagatacagatatcgtttca
 T  S  R  T  G  I  S  M  N  S  D  N  D  L  D  T  D  I  V  S
aatagtgactcagaaaatgacacatatttagatagtgattcagattcagacagtgactca
 N  S  D  S  E  N  D  T  Y  L  D  S  D  S  D  S  D  S  D  S
gattcagatagtgactcagattcagatagtgactcagattcagatagtgactcagattca
 D  S  D  S  D  S  D  S  D  S  D  S  D  S  D  S  D  S  D  S
gacagtgattcagactcagatagtgactcagattcagacagtgattcagactcagatagt
 D  S  D  S  D  S  D  S  D  S  D  S  D  S  D  S  D  S  D  S
gattcagattcagacagtgattcagattcagacagtgactcagactcagacagtgattca
 D  S  D  S  D  S  D  S  D  S  D  S  D  S  D  S  D  S  D  S
gattcagatagtgattcagattcagatagtgattcagattcagatagtgattcagattca
 D  S  D  S  D  S  D  S  D  S  D  S  D  S  D  S  D  S  D  S
gacagtgactcagactcagacagtgattcagattcagatagtgattcagactcagatagt
 D  S  D  S  D  S  D  S  D  S  D  S  D  S  D  S  D  S  D  S
gactcagattcagatagtgattcagactctggtacaagttcaggtaagggttcacatacc
 D  S  D  S  D  S  D  S  G  T  S  S  G  K  G  S  H  T
ggaaaaaaacctggtaaccctaaaggaaatacaaatagaccttctcaaagacatacgaat
 G  K  K  P  G  N  P  K  G  N  T  N  R  P  S  Q  R  H  T  N
caaccccaaaggcctaaatacaatcaaacaaatcaaaacaatataaacaatataaaccat
 Q  P  Q  R  P  K  Y  N  Q  T  N  Q  N  N  I  N  N  I  N  H
aatattaatcatacacgtactagtggagatggtgcgccttttaaacgtcaacaaaatatt
 N  I  N  H  T  R  T  S  G  D  G  A  P  F  K  R  Q  Q  N  I
attaattctaattcaggtcatagaaatcaaaataatataaatcaatttatatggaacaaa
 I  N  S  N  S  G  H  R  N  Q  N  N  I  N  Q  F  I  W  N  K
aatggcttttttaaatctcaaaataataccgaacatagaatgaatagtagcgataatacc
 N  G  F  F  K  S  Q  N  N  T  E  H  R  M  N  S  S  D  N  T
aattcattaattagcagattcagacaattagccacgggtgcttataagtacaatccgttt
 N  S  L  I  S  R  F  R  Q  L  A  T  G  A  Y  K  Y  N  P  F
ttgattaatcaagtaaaaaatttgaatcaattagatggaaaggtgacagatagtgacatt
 L  I  N  Q  V  K  N  L  N  Q  L  D  G  K  V  T  D  S  D  I
```

FIG. 5

```
tatagcttgtttagaaagcaatcatttagaggaaatgaatatttaaattcattacaaaaa
 Y  S  L  F  R  K  Q  S  F  R  G  N  E  Y  L  N  S  L  Q  K
gggacaagctatttcagatttcaatatttta atccacttaattctagtaaatactatgaa
 G  T  S  Y  F  R  F  Q  Y  F  N  P  L  N  S  S  K  Y  Y  E
aatttagatgatcaggttttagctttaattacaggagaaatcggctcaatgccagaactt
 N  L  D  D  Q  V  L  A  L  I  T  G  E  I  G  S  M  P  E  L
aaaaaacctacggataaagaagataaaaatcatagcgccttcaaaaaccatagtgcagat
 K  K  P  T  D  K  E  D  K  N  H  S  A  F  K  N  H  S  A  D
gagataacaacaaataatgatggacactccaaagattatgataagaaaaagaaaatacat
 E  I  T  T  N  N  D  G  H  S  K  D  Y  D  K  K  K  K  I  H
cgaagtctttta tcgttaagtattgcaataattggaattttt ctaggagtcactggacta
 R  S  L  L  S  L  S  I  A  I  I  G  I  F  L  G  V  T  G  L
tatatctttagaagaaaaagtaa
 Y  I  F  R  R  K  K  *
```

FIG. 5 (CONT'D)

MULTICOMPONENT VACCINES

This application is a divisional of application Ser. No. 09/386,959, filed Aug. 31, 1999, now U.S. Pat. No. 6,703,025, issued Mar. 9, 2004, which claims benefit of U.S. Provisional Application No. 60/098,439, filed Aug. 31, 1998.

The present invention was made in part from work supported by grant no. 97-35204-5046 from the United States Department of Agriculture. The U.S. government has certain rights in this invention.

The invention is in the field of biological products for the treatment and diagnosis of bacterial infections.

BACKGROUND OF THE INVENTION

Staphylococci are Gram-positive spherical cells, usually arranged in grape-like irregular clusters. Some are members of the normal flora of the skin and mucous membranes of humans, others cause suppuration, abscess formation, a variety of pyogenic infections, and even fatal septicemia. Pathogenic staphylococci often hemolyze blood, coagulate plasma, and produce a variety of extracellular enzymes and toxins. The most common type of food poisoning is caused by a heat-stable staphylococci enterotoxin.

The genus *Staphylococcus* has at least 30 species. The three main species of clinical importance are *Staphylococcus aureus, Staphylococcus epidermidis,* and *Staphylococcus saprophyticus. Staphylococcus aureus* coagulase-positive, which differentiates it from the other species. *S. aureus* is a major pathogen for humans. Almost every person has some type of *S. aureus* infection during a lifetime, ranging in severity from food poisoning or minor skin infections to severe life-threatening infections. The coagulase-negative staphylococci are normal human flora which sometimes cause infection, often associated with implanted devices, especially in very young, old and immunocompromised patients. Approximately 75% of the infections caused by coagulase-negative staphylococci are due to *S. epidermidis*. Infections due to *Staphylococcus warneri, Staphylococcus hominis,* and other species are less common. *S. saprophyticus* is a relatively common cause of urinary tract infections in young women. The staphylococci produce catalase, which differentiates them from the streptococci.

*S. aureus* colonization of the articular cartilage, of which collagen is a major component, within the joint space appears to be an important factor contributing to the development of septic arthritis. Hematogenously acquired bacterial arthritis remains a serious medical problem. This rapidly progressive and highly destructive joint disease is difficult to eradicate. Typically, less than 50% of the infected patients fail to recover without serious joint damage. *S. aureus* is the predominant pathogen isolated from adult patients with hematogenous and secondary osteomyelitis.

In hospitalized patients, *Staphylococcus* bacteria such as *S. aureus* are a major cause of infection. Initial localized infections of wounds or indwelling medical devices can lead to more serious invasive infections such as septicemia, osteomyelitis, mastitis and endocarditis. In infections associated with medical devices, plastic and metal surfaces become coated with host plasma and matrix proteins such as fibrinogen and fibronectin shortly after implantation. The ability of *S. aureus* and other staphylococcal bacteria to adhere to these proteins is essential to the initiation of infection. Vascular grafts, intravenous catheters, artificial heart valves, and cardiac assist devices are thrombogenic and prone to bacterial colonization. Of the staphylococcal bacteria, *S. aureus* is generally the most damaging pathogen of such infections.

A significant increase in *S. aureus* isolates that exhibit resistance to most of the antibiotics currently available to treat infections has been observed in hospitals throughout the world. The development of penicillin to combat *S. aureus* was a major advance in infection control and treatment. Unfortunately, penicillin-resistant organisms quickly emerged and the need for new antibiotics was paramount. With the introduction of every new antibiotic, *S. aureus* has been able to counter with β-lactamases, altered penicillin-binding proteins, and mutated cell membrane proteins allowing the bacterium to persist. Consequently, methicillin-resistant *S. aureus* (MRSA) and multidrug resistant organisms have emerged and established major footholds in hospitals and nursing homes around the world. (Chambers, H. F., *Clin Microbiol Rev,* 1:173, 1988; and Mulligan, M. E., et al., *Am J Med,* 94:313, 1993) Today, almost half of the staphylococcal strains causing nosocomial infections are resistant to all antibiotics except vancomycin, and it appears to be only a matter of time before vancomycin will become ineffective as well.

There is a strong and rapidly growing need for therapeutics to treat infections from staphylococci such as *S. aureus* which are effective against antibiotic resistant strains of the bacteria. The U.S. National Institutes for Health has recently indicated that this goal is now a national priority.

MSCRAMMs

Bacterial adherence to host tissue occurs when specific microbial surface adhesins termed MSCRAMMs (Microbial Surface Components Recognizing Adhesive Matrix Molecules) specifically recognize and bind to extracellular matrix (ECM) components, such as fibronectin, fibrinogen, collagen, and elastin. Many pathogenic bacteria have been shown to specifically recognize and bind to various components of the ECM in an interaction which appears to represent a host tissue colonization mechanism. This adherence involves a group of bacterial proteins termed MSCRAMMs (Patti, J., et al., *Ann Rev Microbiol,* 48:585-617, 1994; Patti, J. and Hook, M., *Cur Opin Cell Biol.,* 6:752-758, 1994).

MSCRAMMs on the bacterial cell surface and ligands within the host tissue interact in a lock and key fashion resulting in the adherence of bacteria to the host. Adhesion is often required for bacterial survival and helps bacteria evade host defense mechanisms and antibiotic challenges. Once the bacteria have successfully adhered and colonized host tissues, their physiology is dramatically altered and damaging components such as toxins and enzymes are secreted. Moreover, the adherent bacteria often produce a biofilm and quickly become resistant to the killing effect of most antibiotics.

A bacterium can express MSCRAMMs that recognize a variety of matrix proteins. Ligand-binding sites in MSCRAMMs appear to be defined by relatively short contiguous stretches of amino acid sequences (motifs). Because a similar motif can be found in several different species of bacteria, it appears as though these functional motifs are subjected to interspecies transfer (Patti and Hook, *Curr Opin Cell Biol,* 6:752-758, 1994). In addition, a single MSCRAMM can sometimes bind several ECM ligands.

Vaccination Studies

Historically, studies on bacterial adherence have focused primarily on Gram-negative bacteria, which express a wide variety of fimbrial adhesive proteins (designated adhesins) on their cell surface (Falkow, S., *Cell,* 65:1099-1102, 1991). These adhesins recognize specific glycoconjugates exposed on the surface of host cells (particularly epithelial layers).

Employing the lectin-like structures in attachment allows the microorganism to efficiently colonize the epithelial surfaces. This provides the bacteria an excellent location for replication and also the opportunity to disseminate to neighboring host tissues. It has been demonstrated that immunization with pilus adhesins can elicit protection against microbial challenge, such as in *Hemophilus influenza* induced otitis media in a chinchilla model (Sirakova et al., *Infect Immun*, 62(5): 2002-2020, 1994), *Moraxella bovis* in experimentally induced infectious bovine keratoconjunctivitis (Lepper et al., *Vet Microbiol*, 45(2-3):129-138, 1995), and *E coli* induced diarrhea in rabbits (McQueen et al, *Vaccine*, 11:201-206, 1993). In most cases, immunization with adhesins leads to the production of immune antibodies that prevent infection by inhibiting bacterial attachment and colonization, as well as enhancing bacterial opsonophagocytosis and antibody-dependent complement-mediated killing.

The use of molecules that mediate the adhesion of pathogenic microbes to host tissue components as vaccine components is emerging as an important step in the development of future vaccines. Because bacterial adherence is the critical first step in the development of most infections, it is an attractive target for the development of novel vaccines. An increased understanding of the interactions between MSCRAMMs and host tissue components at the molecular level coupled with new techniques in recombinant DNA technology have laid the foundation for a new generation of subunit vaccines. Entire or specific domains of MSCRAMMs, either in their native or site-specifically altered forms, can now be produced. Moreover, the ability to mix and match MSCRAMMs from different microorganisms creates the possibility of designing a single vaccine that will protect against multiple bacteria.

Recent clinical trials with a new subunit vaccine against whooping cough, consisting of the purified *Bordatella pertussis* MSCRAMMs filamentous hemagglutinin and pertactin, in addition to an inactivated pertussis toxin, are a prime example of the success of this type of approach. Several versions of the new acellular vaccine were shown to be safe and more efficacious than the old vaccine that contained whole bacterial cells (Greco et al., *N Eng J Med*, 334:341-348, 1996; Gustaffson et al., *N Eng J Med*, 334:349-355, 1996).

Natural immunity to *S. aureus* infections remains poorly understood. Typically, healthy humans and animals exhibit a high degree of innate resistance to *S. aureus* infections. Protection is attributed to intact epithelial and mucosal barriers and normal cellular and humoral responses. Titers of antibodies to *S. aureus* components are elevated after severe infections (Ryding et al., *J Med Microbiol*, 43(5):328-334, 1995), however to date there is no serological evidence of a correlation between antibody titers and human immunity.

Over the past several decades live, heat-killed, and formalin fixed preparations of *S. aureus* cells have been tested as vaccines to prevent staphylococcal infections. A multicenter clinical trial was designed to study the effects of a commercial vaccine, consisting of a *staphylococcus* toxoid and whole killed staphylococci, on the incidence of peritonitis, exit site infection, and *S. aureus* nasal carriage among continuous peritoneal dialysis patients (Poole-Warren et al., *Clin Nephrol.*, 35:198-206, 1991). Although immunization with the vaccine elicited an increase in the level of specific antibodies to *S. aureus*, the incidence of peritonitis was unaffected. Similarly, immunization of rabbits with whole cells of *S. aureus* could not prevent or modify any stage in the development of experimental endocarditis, reduce the incidence of renal abscess, or lower the bacterial load in infected kidneys (Greenberg, D. P., et al., *Infect Immun*, 55:3030-3034, 1987).

Currently there is no FDA approved vaccine for the prevention of *S. aureus* infections. However, a *S. aureus* vaccine (StaphVAX), based on capsular polysaccharide, is currently being developed by NABI (North American Biologicals Inc.). This vaccine consists of type 5 or type 8 capsular polysaccharides conjugated to *Pseudomonas aeruginosa* exotoxin A (rEPA). The vaccine is designed to induce type-specific opsonic antibodies and enhance opsonophagocytosis (Karakawa et al., *Infect Immun*, 56:1090-1095, 1988). Using a refined lethal challenge mouse model (Fattom et al., *Infect Immun*, 61:1023-1032, 1993) it has been shown that intraperitoneal infusion of type 5 capsular polysaccharide specific IgG reduces the mortality of mice inoculated intraperitoneally with *S. aureus*. The type 5 capsular polysaccharide-rEPA vaccine has also been used to vaccinate seventeen patients with end-stage renal disease (Welch et al., *J Amer Soc Nephrol*, 7(2):247-253, 1996). Geometric mean (GM) IgG antibody levels to the type 5 conjugate increased between 13 and 17-fold after the first immunization, however no additional increases could be detected after additional injections. Interestingly, the GM IgM levels of the vaccinated patients were significantly lower than control individuals. Supported by the animal studies, the vaccine has recently completed a Phase II trial in continuous ambulatory peritoneal dialysis patients. The clinical trial showed the vaccine to be safe but ineffective in preventing staphylococcal infections (NABI SEC FORM 10-K405, Dec. 31, 1995). Two possible explanations for the inability of StaphVAX to prevent infections related to peritoneal dialysis in vaccinated patients are that the immunogenicity of the vaccine was too low due to suboptimal vaccine dosing or that antibodies in the bloodstream are unable to affect infection in certain anatomic areas, such as the peritoneum.

Gram-positive bacteria related sepsis is on the increase. In fact between one-third and one-half of all cases of sepsis are caused by Gram-positive bacteria, particularly *S. aureus* and *S. epidermidis*. In the United States, it can be estimated that over 200,000 patients will develop Gram-positive related sepsis this year.

Using a mouse model (Bremell et al., *Infect Immun.* 59(8): 2615-2623, 1991), it has been clearly demonstrated that active immunization with M55 domain of the Col-binding MSCRAMM can protect mice against sepsis induced death. Mice were immunized subcutaneously with either M55 or a control antigen (bovine serum albumin) and then challenged intravenously with *S. aureus*. Eighty-three percent (35/42) of the mice immunized with M55 survived compared to only 27% of the BSA immunized mice (12/45). This a compilation of 3 separate studies.

Schennings, et al., demonstrated that immunization with fibronectin binding protein from *S. aureus* protects against experimental endocarditis in rats (*Micro Pathog*, 15:227-236, 1993). Rats were immunized with a fusion protein (gal-FnBP) encompassing beta-galactosidase and the domains of fibronectin binding protein from *S. aureus* responsible for binding to fibronectin. Antibodies against fusion protein gal-FnBP were shown to block the binding of *S. aureus* to immobilized fibronectin in vitro. Endocarditis in immunized and non-immunized control rats was induced by catheterization via the right carotid artery, resulting in damaged aortic heart valves which became covered by fibrinogen and fibronectin. The catheterized rats were then infected intravenously with $1 \times 10^5$ cells of *S. aureus*. The number of bacteria associated with aortic valves was determined 11/2 days after the challenge infection and a significant difference in bacterial numbers between immunized and non-immunized groups was then observed.

A mouse mastitis model was used by Mamo, et al., (*Vaccine*, 12:988-992, 1994) to study the effect of vaccination with fibrinogen binding proteins (especially FnBP-A) and collagen binding protein from *S. aureus* against challenge infection with *S. aureus*. The mice vaccinated with fibrinogen binding proteins showed reduced rates of mastitis compared with controls. Gross examination of challenged mammary glands of mice showed that the glands of mice immunized with fibrinogen binding proteins developed mild intramammary infection or had no pathological changes compared with glands from control mice. A significantly reduced number of bacteria could be recovered in the glands from mice immunized with fibrinogen binding proteins as compared with controls. Mamo then found that vaccination with FnBP-A combined with staphylococcal alpha toxoid did not improve the protection (Mamo, et al., *Vaccine*, 12:988-992, 1994). Next, Mamo, et al., immunized mice with only collagen binding protein, which did not induce protection against the challenge infection with *S. aureus*.

Whole killed staphylococci were included in a vaccine study in humans undergoing peritoneal dialysis (Poole-Warren et al., *Clin. Nephrol*, 35:198-206, 1991). In this clinical trial, a commercially available vaccine of alpha-hemolysin toxoid combined with a suspension of whole killed bacteria) was administered intramuscularly ten times over 12 months, with control patients receiving saline injections. Vaccination elicited significant increases in the levels of antibodies to *S. aureus* cells in the peritoneal fluid and to alpha-hemolysin in the serum. However, immunization did not reduce the incidences of peritonitis, catheter-related infections or nasal colonization among vaccine recipients. The lack of protective efficacy in this trial were attributed to a suboptimal vaccine formulation.

Secreted proteins have been explored as components of subcellular vaccines. The alpha toxin is among the most potent staphylococcal exotoxins; it has cytolytic activity, induces tissue necrosis and kills laboratory animals. Immunization with formaldehyde-detoxified alpha toxin does not protect animals from systemic or localized infections, although it may reduce the clinical severity of the infections (Ekstedt, R. D., in *The Staphylococci*, 385-418, 1972).

One study has evaluated the protective efficacy of antibodies to the *S. aureus* microcapsule in an experimental model of staphylococcal infection (Nemeth, J. and Lee, J. C., *Infect. Immun.* 63:375-380, 1995). Rats were actively immunized with killed, microencapsulated bacteria or passively immunized with high-titer rabbit antiserum specific for the capsular polysaccharide. Control animals were injected with saline or passively immunized with normal rabbit serum. Protection against catheter-induced endocarditis resulting from intravenous challenge with the same strain was then evaluated. Despite having elevated levels of anticapsular antibodies, the immunized animals were susceptible to staphylococcal endocarditis and immunized and control animals had similar numbers of bacteria in the blood.

As described in the Detailed Description of the Invention hereinbelow, a number of patents and patent applications describe the gene sequences for fibronectin, fibrinogen, collagen, elastin, and MHC II analogous type binding proteins. These patents and patent applications are incorporated by reference in their entirety. These documents teach that the proteins, fragments, or antibodies immunoreactive with those proteins or fragments can be used in vaccinations for the treatment of *S. aureus* infections. PCT/US97/087210 discloses the vaccination of mice with a combination of a collagen binding protein (M55 fragment), a fibronectin binding peptide (formulin treated FnBP-A (D1-D3)) and a fibrinogen binding peptide (ClfA).

The lack of adequate protection against staphylococcal infection that has been seen to date from the vaccines described above is likely the result of the failure to generate the proper immune response, perhaps along with improper immunization scheduling or an improper immunization route. Additional factors that also contribute to the poor performance of past vaccines can be reflected in the fact that staphylococcal bacteria such as *S. aureus* have been observed to temporally regulate the expression of most of its virulence factors via regulatory genes loci agr and sar. For example, *S. aureus* contains two genes that encode cell surface fibrinogen binding proteins, ClfA and ClfB. Interestingly, ClfA is predominately expressed in early exponential growth, while ClfB is expressed later in the growth phase. Accordingly, the antigens that the invading organism presents to the host in vivo may not be the same as those used in the vaccine. In addition, not every *S. aureus* antigen is expressed on every isolate. For example, only about 50% of *S. aureus* clinical isolates express the gene cna, which encodes for the collagen binding MSCRAMM. To generate an effective immunotherapeutic against *S. aureus*, the vaccine must be multi-component and contain antigens that span the growth cycle as well as include antigens that are expressed by a majority of *S. aureus* isolates.

Despite the advances in the art of compositions for the treatment of infections from staphylococcal bacteria such as *S. aureus*, there remains a need to provide a more effective product, and preferably one that exhibits a broad spectrum immunization against staphylococcal bacteria of various strains, and to particular proteins which may be expressed at different stages of the bacterial growth phase.

Therefore, it is an object of the invention to provide a new therapeutic composition for immunization against infections from staphylococcal bacteria such as *S. aureus* and *S. epidermidis*.

It is another object of the present invention to provide a vaccine that will provide protection against mastitis, arthritis, endocarditis, septicemia, and osteomyelitis, furunculosis, cellulitis, pyemia, pneumonia, pyoderma, supporation of wounds, food poisoning, bladder infections and other infectious diseases.

It is another object of the present invention to provide a therapeutic composition that immunizes against staphylococcal infection, enhances the amount of intracellular killing of staphylococcal bacteria, and increases the rate of phagocytosis of staphylococcal bacteria.

It is still another object of the present invention to provide a composition that will further protect the host by neutralizing exotoxins.

SUMMARY OF THE INVENTION

It has been discovered that the treatment of staphylococcal infections can be significantly enhanced by immunization with certain selected combinations of bacterial binding proteins or fragments thereof, or antibodies to those proteins or fragments. The proteins or fragments can be used in active vaccines, and the antibodies in passive vaccines. Alternatively, the combinations can be used to select donor blood pools for the preparation of purified blood products for passive immunization. By careful selection of the proteins, fragments, or antibodies, a vaccine is provided that imparts protection against a broad spectrum of *Staphylococcus* bacterial strains and against proteins that are expressed at different stages of the logarithmic growth curve.

The vaccine and products described herein respond to the urgent need of the medical community for a substitute for small molecule antibiotics, which are rapidly losing effectiveness. The vaccines are a significant improvement over the prior art, which while generally teaching the use of MSCRAMMs to impart immunization, did not teach which combinations of the large number of known MSCRAMMs should be used to impart superior protection.

In one embodiment of the invention, a composition is provided that includes at least a collagen binding protein or peptide (or an appropriate site directed mutated sequence thereof) such as CNA, or a protein or fragment with sufficiently high homology thereto, in combination with a fibrinogen binding protein, preferably Clumping factor A ("ClfA") or Clumping factor B ("ClfB"), or a useful fragment thereof or a protein or fragment with sufficiently high homology thereto.

In another embodiment of the invention, a composition is provided that includes at least a fibronectin binding protein or peptide (or an appropriate site directed mutated sequence thereof), or a protein or fragment with sufficiently high homology thereto, in combination with the fibrinogen binding protein, preferably A or B (ClfA or ClfB, respectively), or a useful fragment thereof or a protein or fragment with sufficiently high homology thereto.

In a third embodiment, a composition is provided that includes at least the fibrinogen binding protein A (ClfA) and the fibrinogen binding protein B (ClfB), or useful fragments thereof or a protein or fragment with sufficiently high homology thereto.

In a fourth embodiment, a composition is provided that includes at least a fibronectin binding protein or peptide (or an appropriate site directed mutated sequence thereof), or a protein or fragment with sufficiently high homology thereto, in combination with (i) the fibrinogen binding protein A and B (ClfA and ClfB), or a useful fragment thereof or a protein or fragment with sufficiently high homology thereto; and (ii) a collagen binding protein or useful fragment thereof.

In an additional embodiment, a composition is provided that includes the components of the prior embodiments in combination with an elastin binding protein or peptide or a protein or fragment with sufficiently high homology thereto.

In another embodiment, a composition is provided that includes the components of the prior embodiments in combination with a MHC II analogous protein or peptide or a protein or fragment with sufficiently high homology thereto.

In another embodiment, a composition is provided that includes the components of any of the prior combinations in combination with a bacterial component to increase the rate of phagocytosis of the staphylococcal bacteria. In a one such embodiment, the bacterial component comprises a capsular polysaccharide, such as capsular polysaccharide type 5 or type 8.

In an additional embodiment, a composition is provided that includes any of the prior combinations in combination with the extracellular matrix-binding proteins SdrC, SdrD, SdrE or a consensus or variable sequence amino acid motif, or useful fragments thereof or proteins or fragments with sufficiently high homology thereto.

In an additional embodiment, a composition is provided that includes and of the prior combinations in combination with the extracellular matrix-binding proteins SdrF, SdrG, or SdrH, or a consensus or variable sequence amino acid motif, or useful fragments thereof or proteins or fragments with sufficiently high homology thereto. This embodiment is particularly effective in developing vaccines that can be useful with regard to both coagulase-positive and coagulase-negative staphylococcal bacteria.

In another embodiment, a composition is provided that includes at least the extracellular matrix-binding proteins SdrC, SdrD and SdrE or useful fragments thereof, such as the consensus or variable sequence amino acid motif, or a protein or fragment with sufficiently high homology thereto.

Alternatively, compositions are provided that include monoclonal or polyclonal antibodies which are immunoreactive to the selected combination of described components. These compositions can be used in vaccinations to treat patients infected with *Staphylococcus* infections.

In other embodiments of the invention, the combinations of proteins, fragments or antibodies as described are used in diagnostic kits.

As described below, proteins and peptides to be used in the composition which bind to fibronectin, fibrinogen, collagen, and elastin are known. Alternatively, one can identify new fibronectin, fibrinogen, collagen, and elastin binding proteins, or the epitopes thereof for use in the composition. Methods of identifying a peptide of a binding domain of a binding protein that binds to the ligand of choice are known. For example, one can contact a candidate protein or peptide with the ligand under conditions effective to allow binding of the ligand to the binding domain of a binding protein, and identify a positive candidate peptide that binds to the ligand.

Antibodies that bind to the binding domains of the composition proteins or peptides can be generated by administering to an animal a pharmaceutical composition comprising an immunologically effective amount of the combination of proteins or peptides, even though the peptide does not specifically bind to the ECM.

The combination of the isolated, recombinant or synthetic MSCRAMM proteins, or active fragments thereof or fusion proteins thereof, are also useful as scientific research tools to identify staphylococcal binding sites on the host ECM molecules, thereby promoting an understanding of the mechanisms of bacterial pathology and the development of antibacterial therapies. Furthermore, the isolated, recombinant or synthetic proteins, or antigenic portions thereof (including epitope-bearing fragments), or fusion proteins thereof can be administered to animals as immunogens or antigens, alone or in combination with an adjuvant, for the production of antisera reactive with MSCRAMM proteins. In addition, the proteins can be used to screen antisera for hyperimmune patients from whom can be derived antibodies having a very high affinity for the proteins. Antibodies isolated from the antisera are useful for the specific detection of staphylococcal bacteria or binding proteins, as research tools, or as therapeutic treatments against staphylococcal infection.

The proteins, or active fragments thereof, and antibodies to the proteins are useful for the treatment of infections from staphylococcal infections from bacteria such as *S. aureus* as described above; for the development of anti-Staphylococcus vaccines for active or passive immunization; and, when administered as pharmaceutical composition to a wound or used to coat medical devices or polymeric biomaterials in vitro and in vivo, both the proteins and the antibodies are useful as blocking agents to prevent or inhibit the binding of staphylococcal bacteria to the wound site or biomaterials.

Preferably, animal derived antibody is modified so that it is less immunogenic in the patient to whom it is administered. For example, if the patient is a human, the antibody may be "humanized" by transplanting the complimentarily determining regions of the hybridoma-derived antibody into a human monoclonal antibody as described by Jones et al., (Nature 321:522-525 (1986)) or Tempest et al. (*Biotechnology* 9:266-273 (1991)).

Kits are also provided that are useful as a diagnostic agent for the detection of staphylococcal infections. According to yet another embodiment, anti-MSCRAMM antibodies as well as the MSCRAMM polypeptides of this invention, are useful as diagnostic agents for detecting infection by staphylococcal bacteria, because the polypeptides are capable of binding to antibody molecules produced in animals, including humans that are infected with staphylococcal bacteria such as *S. aureus*, and the antibodies are capable of binding to particular staphylococcal bacteria or antigens thereof.

Diagnostic agents may be included in a kit which can also include instructions for use and other appropriate reagents. The kit can also contain a means to evaluate the product of the assay, for example, a color chart, or numerical reference chart. The polypeptide or antibody may be labeled with a detection means that allows for the detection of the MSCRAMM polypeptide when it is bound to an antibody, or for the detection of the anti-MSCRAMM polypeptide antibody when it is bound to *Staphylococcus* bacteria.

The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}$I or $^{51}$Cr that produces gamma ray emissions, or a radioactive element that emits positrons which produce gamma rays upon encounters with electrons present in the test solution, such as $^{11}$C, $^{15}$O, or $^{13}$N. The linking of the detection means is well known in the art. For instance, monoclonal anti-MSCRAMM polypeptide antibody molecules produced by a hybridoma can be metabolically labeled by incorporation of radioisotope-containing amino acids in the culture medium, or polypeptides may be conjugated or coupled to a detection means through activated functional groups.

The diagnostic kits of the present invention may be used to detect the presence of a quantity of *Staphylococcus* bacteria or anti-*Staphylococcus* antibodies in a body fluid sample such as serum, plasma or urine. Thus, in preferred embodiments, an MSCRAMM polypeptide or anti-MSCRAMM polypeptide antibody composition of the present invention is bound to a solid support typically by adsorption from an aqueous medium. Useful solid matrices are well known in the art, and include crosslinked dextran; agarose; polystyrene; polyvinylchloride; cross-linked polyacrylamide; nitrocellulose or nylon-based materials; tubes, plates or the wells of microtiter plates. The polypeptides or antibodies of the present invention may be used as diagnostic agents in solution form or as a substantially dry powder, e.g., in lyophilized form.

BRIEF DESCRIPTION OF THE DRAWING FIGURES

FIG. 1 is a schematic representation of the peptides used in illustrative vaccine, MSCRAMM IV. This drawing illustrates the essential features of the collagen binding MSCRAMM CNA, fibrinogen binding MSCRAMM ClfA, fibrinogen binding MSCRAMM ClfB and fibronectin binding MSCRAMM FnBPA proteins. The MSCRAMMs are shown with regions denoted that were expressed as recombinant proteins and used to generate antibodies in rabbits immunized with MSCRAMM IV. All proteins were designed with an amino terminal histidine tag to facilitate purification by metal chelating chromatography.

FIG. 2 is a time course graph of the immune response in MCSCRAMM vaccinated Rhesus Monkeys as shown by changes in antibody titers against the MSCRAMMs CNA, ClfA, ClfB and FnBPA, respectively. The titers were analyzed by ELISA and measured as changes in absorbance (quantified at 405 nm) during each week over the course of a six-month period of treatment following the original immunization with the antigen.

FIG. 3 shows the nucleic acid sequence coding for the sdrF gene from *S. epidermidis*, identified as SEQ ID NO: 1 and the amino acid sequence coded thereby, identified as SEQ ID NOS: 2-6.

FIG. 4 shows the nucleic acid sequence coding for the sdrG gene from *S. epidermidis*, identified as SEQ ID NO: 7 and the amino acid sequence coded thereby, identified as SEQ ID NOS: 8-12.

FIG. 5 shows the nucleic acid sequence coding for the sdrH gene from *S. epidermidis*, identified as SEQ ID NO: 13 and the amino acid sequence coded thereby, identified as SEQ ID NO: 14.

DETAILED DESCRIPTION OF THE INVENTION

Figure 1:
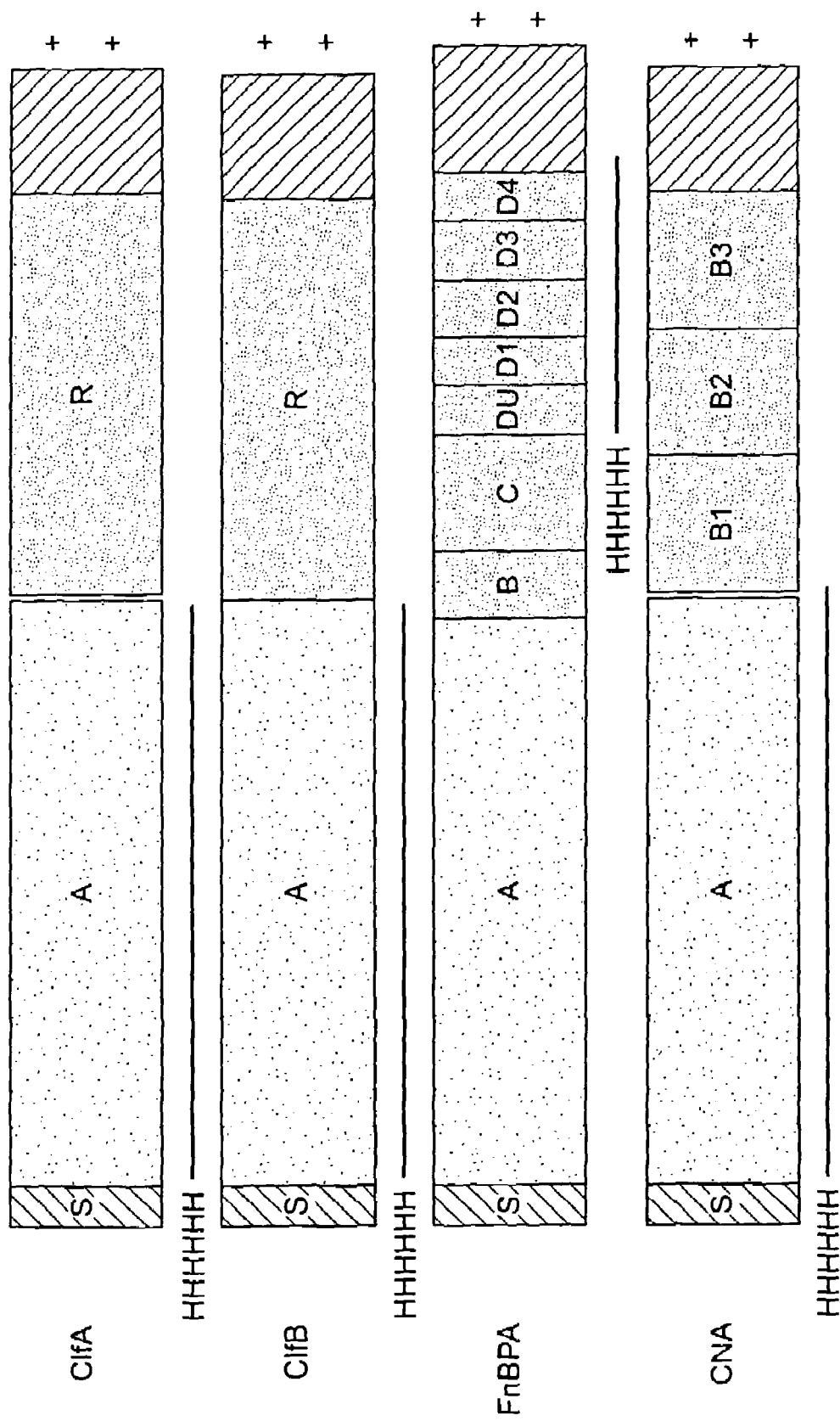

Compositions suitable for use as vaccines are provided that include at least:

(i) A collagen binding protein, peptide or domain (or an appropriate site directed mutated sequence thereof such as CNA, or a protein, fragment or domain with sufficiently high homology thereto, in combination with a fibrinogen binding protein, preferably Clumping factor A ("ClfA") or Clumping factor B ("ClfB"), or a useful fragment thereof or a protein or fragment with sufficiently high homology thereto;

(ii) a fibronectin binding protein or peptide (or an appropriate site directed mutated sequence thereof, or a protein or fragment with sufficiently high homology thereto, in combination with the fibrinogen binding proteins A and B (ClfA and ClfB), or useful fragments thereof or proteins or fragments with sufficiently high homology thereto; or (iii) the fibrinogen binding protein A (ClfA) and the fibrinogen binding protein B (ClfB), or useful fragments thereof or a protein or fragment with sufficiently high homology thereto; or (iv) fibronectin binding protein or peptide (or an appropriate site directed mutated sequence thereof), or a protein or fragment with sufficiently high homology thereto, in combination with the fibrinogen binding protein A and B (ClfA and ClfB), or a useful fragment thereof or a protein or fragment with sufficiently high homology thereto; and a collagen binding protein or useful fragment thereof, or a protein or fragment with sufficiently high homology thereto;

(v) components of any of the above embodiments in combination with an elastin binding protein or peptide or a protein or fragment with sufficiently high homology thereto; or (vi) components of any of the above embodiments in combination with a MHC II analogous type binding protein or peptide, protein or fragment with sufficiently high homology thereto; or (vi) components of any of the above embodiments in combination with a bacterial component to increase the rate of phagocytosis of a staphylococcal bacteria such as *S. aureus*; or (vii) components of any of the above embodiments in combination with the extracellular matrix-binding proteins SdrC, SdrD or SdrE, or useful fragments thereof, such as a consensus or variable sequence amino acid motif, or proteins or fragments with sufficiently high homology thereto; or (viii) components of any of the above embodiments in combination with the extracellular matrix-binding proteins SdrF, SdrG or SdrH or useful fragments thereof, such as a consensus or variable sequence amino acid motif, or proteins or fragments with sufficiently high homology thereto, such that a vaccine created from said components will also be useful to immunize a patient against infection from coagulase-negative bacteria such as *S. epidermidis* as well as coagulase positive bacteria such as *S. aureus*; or (ix) the extracellular matrix-binding proteins SdrC, SdrD and SdrE or useful fragments thereof, such as a consensus or variable sequence amino acid motif, or a protein or fragment with sufficiently high homology thereto.

Isolated protein fragments from wild-type or naturally occurring variants or synthetic or recombinant peptides corresponding to wild-type, naturally occurring variants or introduced mutations that do not correspond to a naturally occurring binding domain of a binding protein can be used in these embodiments.

The isolated peptides should be of a sufficient length to allow for the generation of an antibody that binds both to the isolated peptide and the binding domain, and blocks the binding of the binding protein to its ligand. In certain aspects, peptides comprising at least about 5, about 6, about 7, about 8, about 9, about 10, about 11, about 12, about 13, about 14, about 15, about 16, about 17, about 18, about 19, about 20, about 22, about 24, about 25, about 30, about 35, about 40, about 45 or about 50 contiguous amino acids are preferred. In other preferred aspects of the invention, the isolated peptide comprises at least about 6 contiguous amino acids from the wild type sequence of the binding domain.

In one aspect of the invention, the isolated peptide or antibody compositions are used to generate an immunological response in an animal. In this aspect, the compositions preferably further comprise an adjuvant. Many adjuvants are known for use in vaccinations and are readily adapted to this composition. The isolated peptide or protein composition is preferably dispersed in a pharmaceutically acceptable excipient.

The isolated peptide can be linked to a selected amino acid sequence to make a fusion protein. As a nonlimiting example, a fusion protein can be made that comprises at least a first peptide of a binding domain of a binding protein operatively linked to a selected amino acid sequence. In one embodiment, if the peptide is a fibronectin binding domain, the first peptide does not specifically bind to fibronectin. In preferred aspects, the first peptide is linked to a selected carrier molecule or amino acid sequence, including, but not limited to, keyhole limpet hemocyanin (KLH) and bovine serum albumin (BSA).

Immunological compositions, including vaccine, and other pharmaceutical compositions containing the selected MSCRAMM proteins or the DNA encoding such MSCRAMM proteins are included within the scope of the present invention. The combination of binding proteins, or active or antigenic fragments thereof, or fusion proteins thereof can be formulated and packaged, alone or in combination with other antigens, using methods and materials known to those skilled in the art for vaccines. The immunological response may be used therapeutically or prophylactically and may provide antibody immunity or cellular immunity such as that produced by T lymphocytes such as cytotoxic T lymphocytes or CD4+ T lymphocytes.

Vaccines can be prepared for use in both active and passive immunizations. Preferably the antigenic material is extensively dialyzed to remove undesired small molecular weight molecules and/or lyophilized for more ready formulation into a desired vehicle.

I. DEFINITIONS

The terms FnBP-A protein, FnBP-B protein, ClfA protein, ClfB protein, SdrC protein, SdrD protein, SdrE protein, SdrF protein, SdrG protein, SdrH protein, CNA protein, EbpS protein and MHCII protein are defined herein to include FnBP-A, FnBP-B, ClfA, ClfB, SdrC, SdrD, SdrE, SdrF, SdrG, SdrH, CNA, EbpS and MHCII subdomains, respectively, active or antigenic fragments of FnBP-A, FnBP-B, ClfA, ClfB, SdrC, SdrD, SdrE, SdrF, SdrG, SdrH, CNA, EbpS and MHCII proteins, and proteins or fragments that have sufficiently high homology therewith. Active fragments of FnBP-A, FnBP-B, ClfA, ClfB, SdrC, SdrD, SdrE, SdrF, SdrG, SdrH, CNA, EbpS and MHCII proteins are defined herein as peptides or polypeptides capable of blocking the binding of *Staphylococcus* bacteria to host ECM. Antigenic fragments of FnBP-A, FnBP-B, ClfA, ClfB, SdrC, SdrD, SdrE, SdrF, SdrG, SdrH, CNA, EbpS and MHCII proteins are defined herein as peptides or polypeptides capable of producing an immunological response.

The term "adhesin" as used herein includes naturally occurring and synthetic or recombinant proteins and peptides which can bind to extracellular matrix proteins and/or mediate adherence to host cells.

The term "amino acid" as used herein includes naturally occurring and synthetic amino acids and includes, but is not limited to, alanine, valine, leucine, isoleucine, proline, phenylalanine, tryptophan, methionine, glycine, serine, threonine, cysteine, tyrosine, asparagine, glutamate, aspartic acid, glutamic acid, lysine, arginine, and histidine.

An "antibody" is any immunoglobulin, including antibodies and fragments thereof, that binds a specific epitope. The term as used herein includes monoclonal antibodies, polyclonal, chimeric, single chain, bispecific, simianized, and humanized-antibodies as well as Fab fragments, including the products of an Fab immunoglobulin expression library.

The phrase "antibody molecule" in its various grammatical forms as used herein contemplates both an intact immunoglobulin molecule and an immunologically active portion of an immunoglobulin molecule.

As used herein, an "antigenically functional equivalent" protein or peptide is one that incorporates an epitope that is immunologically cross-reactive with one or more epitopes either derived from any of the particular MSCRAMM proteins disclosed (e.g., FnB-B, FnB-A, FnBP-B and FnBP-A) or derived from any of the particular bacterial components disclosed (e.g., teichoic acids, alpha toxin and capsular polysaccharide type 5). Antigenically functional equivalents, or epitopic sequences, may be first designed or predicted and then tested, or may simply be directly tested for cross-reactivity.

As used herein, "pg" means picogram, "ng" means nanogram, "ug" or "μg" mean microgram, "mg" means milligram, "ul" or "μl" mean microliter, "ml" means milliliter, "l" means liter.

A "cell line" is a clone of a primary cell that is capable of stable growth in vitro for many generations.

A "clone" is a population of cells derived from a single cell or common ancestor by mitosis.

A DNA "coding sequence" is a double-stranded DNA sequence which is transcribed and translated into a polypeptide in vivo when placed under the control of appropriate regulatory sequences. The boundaries of the sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genetic DNA sequences from eukaryotic (e.g., mammalian) DNA, and even synthetic DNA sequences. A polyadenylation signal and transcription termination sequence will usually be located 3' to the coding sequence. "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g, restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA. Transcriptional and translational control sequences are "DNA regulatory sequences", such as promoters, enhancers, polyadenylation signals, terminators, and the like, that provide for the expression of a coding sequence in a host cell.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

As used herein, the term "extracellular matrix proteins," or ECM, refers to four general families of macromolecules, collagens, structural glycoproteins, proteoglycans and elastins, including fibronectin, and fibrinogen, that provide support and modulate cellular behavior.

"Immunologically effective amounts" are those amounts capable of stimulating a B cell and/or T cell response.

As used herein, the term "in vivo vaccine" refers to immunization of animals with proteins so as to elicit a humoral and cellular response that protects against later exposure to the pathogen.

The term "ligand" is used to include molecules, including those within host tissues, to which pathogenic bacteria attach.

The term "MHC II antigens" as used herein refers to cell-surface molecules that are responsible for rapid graft rejections and are required for antigen presentation to T-cells.

The phrase "monoclonal antibody" in its various grammatical forms refers to an antibody having only one species of antibody combining site capable of immunoreacting with a particular antigen.

The term "oligonucleotide," as used herein is defined as a molecule comprised of two or more nucleotides, preferably more than three. Its exact size will depend upon many factors which, in turn, depend upon the ultimate function and use of the oligonucleotide.

As used herein, the phrase "pharmaceutically acceptable" refers to molecular entities and compositions that are physiologically tolerable and do not typically produce an unacceptable allergic or similar untoward reaction when administered to a human.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a noncomplementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to hybridize therewith and thereby form the template for the synthesis of the extension product.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease SI), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A "replicon" is a genetic element (e.g., plasmid, chromosome, virus) that functions as an autonomous unit of DNA replication in vivo; i.e., capable of replication under its own control.

As used herein, the terms "restriction endonucleases" and "restriction enzymes" refer to bacterial enzymes, each of which cut double-stranded DNA at or near a specific palindromic nucleotide sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, the term "site directed mutagen" refers to a compound that can increase the rate at which mutations occur at a certain site within the DNA molecule.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "vector" is a replicon, such as plasmid, phage or cosmid, to which another DNA segment may be attached so as to bring about the replication of the attached segment.

The term "wound" is used herein to mean the epithelial cellular layer, and other surface structures over tissue, damaged by mechanical, chemical or other influence.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments.

The selected combinations of bacterial binding proteins or fragments thereof in the composition used include those binding to fibronectin, fibrinogen, collagen, and elastin. Any such protein, peptide, fragment thereof, or sequence substantially homologous thereto can be used in this invention. Illustrative examples are provided below. In addition, bacterial binding proteins or fragments to MHC II analogous

II. FIBRONECTIN-BINDING MSCRAMMs

Fibronectin (Fn) is a 440-kDa glycoprotein found in the ECM and body fluids of animals. The primary biological function of fibronectin appears to be related to its ability to serve as a substrate for the adhesion of cells expressing the appropriate integrins. Several bacterial species have been shown to bind fibronectin specifically and to adhere to a fibronectin-containing substratum. Most *S. aureus* isolates bind Fn, but do so in varying extents, which reflects variations in the number of MSCRAMM molecules expressed on the bacterial cell surface. The interaction between Fn and *S. aureus* is highly specific (Kuusela, P., *Nature,* 276:718-20, 1978). Fn binding is mediated by two surface exposed proteins with molecular weights of 110 kDa, named FnBP-A and FnBP-B. The primary Fn binding site consists of a motif of 35-40 amino acids, repeated three to five times. The genes for these have been cloned and sequenced (Jonsson, K., et al., *Eur. J. Biochem.,* 202:1041-1048, 1991).

WO-A-85/05553 discloses bacterial cell surface proteins having fibronectin, fibrinogen, collagen, and or laminin binding ability.

U.S. Pat. Nos. 5,320,951 and 5,571,514 to Hook, et al., discloses the fibronectin binding protein A (fnbA) gene sequence, and products and methods based on this sequence.

U.S. Pat. No. 5,175,096 to Hook et al., discloses the gene sequence of fnbB, a hybrid DNA molecule (fnbB) and biological products and methods based on this sequence.

U.S. Pat. No. 5,652,217 discloses an isolated and purified protein having binding activity that is encoded by a hybrid DNA molecule from *S. aureus* of defined sequence.

U.S. Pat. No. 5,440,014 discloses a fibronectin binding peptide within the D3 homology unit of a fibronectin binding protein of *S. aureus* which can be used for vaccination of ruminants against mastitis caused by staphylococcal infections, for treatment of wounds, for blocking protein receptors, for immunization of other animals, or for use in a diagnostic assay.

U.S. Pat. No. 5,189,015 discloses a method for the prophylactic treatment of the colonization of a *S. aureus* bacterial strain having the ability to bind to fibronectin in a mammal that includes administering to the mammal in need of treatment a prophylactically therapeutically active amount of a protein having fibronectin binding properties, to prevent the generation of infections caused by a *S. aureus* bacterial strain having the ability to bind fibronectin, wherein the protein has a molecular weight of 87 kDa to 165 kDa.

U.S. Pat. No. 5,416,021 discloses a fibronectin binding protein encoding DNA from *Streptococcus dysgalactiae*, along with a plasmid that includes DNA encoding for fibronectin binding protein from *S. dysgalactiae* contained in *E. coli*, DNA encoding a fibronectin binding protein from *S. dysgalactiae* and an *E. coli* microorganism transformed by DNA encoding a fibronectin binding protein from *S. dysgalactiae.*

It has been observed that antibodies to wild type fibronectin binding protein do not substantially inhibit the ability of *S. aureus* to bind to fibronectin, and thus do not exhibit a significant therapeutic effect, in vivo. PCT/US98/01222 discloses antibodies that block the binding of fibronectin to fibronectin binding proteins. The antibodies were raised against a site-directed mutated sequence of fibronectin binding protein that does not bind to fibronectin. It was identified that there is a rapid complexation of fibronectin with fibronectin binding proteins and fragments in vivo. Peptide epitopes that do not bind to fibronectin, even though based on a fibronectin binding domain of a fibronectin binding protein, do not form a complex with fibronectin in vivo. This allows antibodies to be made against the uncomplexed peptide epitope, which inhibit or block the binding of fibronectin to fibronectin binding proteins.

III. COLLAGEN-BINDING MSCRAMMs

Collagen is the major constituent of cartilage. Collagen (Cn) binding proteins are commonly expressed by staphylococcal strains. The Cn binding MSCRAMM of *S. aureus* adheres to cartilage in a process that constitutes an important part of the pathogenic mechanism in staphylococcal infections. (Switalski, et al. *Mol. Micro.* 7(1), 99-107, 1993) Cn binding by *S aureus* is found to play a role in at least, but not only, arthritis and septicemia. CNAs with molecular weights of 133, 110 and 87 kDa (Patti, J., et al., *J. Biol. Chem.,* 267:4766-4772, 1992) have been identified. Strains expressing CNAs with different molecular weights do not differ in their Cn binding ability (Switalski, L. M., et al., *Mol. Microbiol.,* 7:99-107, 1993).

Staphylococcal strains recovered from the joints of patients diagnosed with septic arthritis or osteomyelitis almost invariably express a CBP, whereas significantly fewer isolates obtained from wound infections express this adhesin (Switalski et al., *Mol. Microbiol.,* 7:99-107, 1993). Similarly, *S. aureus* strains isolated from the bones of patients with osteomyelitis often have an MSCRAMM recognizing the bone-specific protein, bone sialoprotein (BSP) (Ryden et al., *Lancet,* 11:515-518, 1987). *S. aureus* colonization of the articular cartilage within the joint space appears to be an important factor contributing to the development of septic arthritis.

PCT WO 92/07002 discloses a hybrid DNA molecule which includes a nucleotide sequence from *S. aureus* coding for a protein or polypeptide having collagen binding activity and a plasmid or phage comprising the nucleotide sequence. Also disclosed are an *E. coli* strain expressing the collagen binding protein, a microorganism transformed by the recombinant DNA, the method for producing a collagen binding protein or polypeptide, and the protein sequence of the collagen binding protein or polypeptide.

The cloning, sequencing, and expression of a gene cna, encoding a S. aureus CBP has been reported (Patti, J., et al., J. Biol. Chem., 267:4766-4772, 1992). The cna gene encodes an 133-kDa adhesin that contains structural features characteristic of surface proteins isolated from Gram-positive bacteria.

Recently, the ligand-binding site has been localized within the N-terminal half of the CBP (Patti, J. et al., Biochemistry, 32:11428-11435, 1993). By analyzing the Col binding activity of recombinant proteins corresponding to different segments of the MSCRAMM, a 168-amino-acid long protein fragment (corresponding to amino acid residues 151-318) that had appreciable Col binding activity was identified. Short truncations of this protein in the N or C terminus resulted in a loss of ligand binding activity but also resulted in conformational changes in the protein as indicated by circular dichroism spectroscopy.

Patti et al. (J of Biol Chem., 270, 12005-12011, 1995) disclose a collagen binding epitope in the S. aureus adhesin encoded by the cna gene. In their study, the authors synthesized peptides derived from the sequence of the said protein and used them to produce antibodies. Some of these antibodies inhibit the binding of the protein to collagen.

PCT/US97/08210 discloses that certain identified epitopes of the collagen binding protein (M55, M33, and M17) can be used to generate protective antibodies. The application also discloses the crystal structure of the CBP which provides critical information necessary for identifying compositions which interfere with, or block completely, the binding of Col to CBPS. The ligand-binding site in the S. aureus CBP and a 25-amino-acid peptide was characterized that directly inhibits the binding of S. aureus to 125 I-labeled type II Col.

IV. FIBRINOGEN-BINDING MSCRAMMs

Fibrin is the major component of blood clots, and fibrinogen/fibrin is one of the major plasma proteins deposited on implanted biomaterials. Considerable evidence exists to suggest that bacterial adherence to fibrinogen/fibrin is important in the initiation of device-related infection. For example, as shown by Vaudaux et al., S. aureus adheres to in vitro plastic that has been coated with fibrinogen in a dose-dependent manner (J. Infect. Dis. 160:865-875 (1989)). In addition, in a model that mimics a blood clot or damage to a heart valve, Herrmann et al. demonstrated that S. aureus binds avidly via a fibrinogen bridge to platelets adhering to surfaces (J. Infect. Dis. 167: 312-322 (1993)). S. aureus can adhere directly to fibrinogen in blood clots formed in vitro, and can adhere to cultured endothelial cells via fibrinogen deposited from plasma acting as a bridge (Moreillon et al., Infect. Immun. 63:4738-4743 (1995); Cheung et al., J. Clin. Invest. 87:2236-2245 (1991)). As shown by Vaudaux et al. and Moreillon et al., mutants defective in the fibrinogen-binding protein clumping factor (ClfA) exhibit reduced adherence to fibrinogen in vitro, to explanted catheters, to blood clots, and to damaged heart valves in the rat model for endocarditis (Vaudaux et al., Infect. Immun. 63:585-590 (1995); Moreillon et al., Infect. Immun. 63: 4738-4743 (1995)).

An adhesin for fibrinogen, often referred to as "clumping factor," is located on the surface of S. aureus cells. The interaction between bacteria and fibrinogen in solution results in the instantaneous clumping of bacterial cells. The binding site on fibrinogen is located in the C-terminus of the gamma chain of the dimeric fibrinogen glycoprotein. The affinity is very high and clumping occurs in low concentrations of fibrinogen. Scientists have recently shown that clumping factor also promotes adherence to solid phase fibrinogen, to blood clots, and to damaged heart valves (McDevitt et al., Mol. Microbiol. 11: 237-248 (1994); Vaudaux et al., Infect. Immun. 63:585-590 (1995); Moreillon et al., Infect. Immun. 63: 4738-4743 (1995)).

Two genes in S. aureus have been found that code for two Fg binding proteins, ClfA and ClfB. The gene, clfA, was cloned and sequenced and found to code for a polypeptide of 92 kDa. ClfA binds the gamma chain of fibrinogen, and ClfB binds the alpha and beta chains (Eidhin, et al., Mol Micro, awaiting publication, 1998). ClfB is a cell wall associated protein with a predicted molecular weight of 88 kDa and an apparent molecular weight of 124 kDa that binds both soluble and immobilized fibrinogen and acts as a clumping factor.

The gene for a clumping factor protein, designated ClfA, was cloned, sequenced and analyzed in detail at the molecular level (McDevitt et al., Mol. Microbiol. 11: 237-248 (1994); McDevitt et al., Mol Microbiol 16:895-907 (1995)). The predicted protein is composed of 933 amino acids. A signal sequence of 39 residues occurs at the N-terminus followed by a 520 residue region (region A), which contains the fibrinogen binding domain. A 308 residue region (region R), composed of 154 repeats of the dipeptide serine-aspartate, follows. The R region sequence is encoded by the 18 basepair repeat GAY TCN GAY TCN GAY AGY (SEQ ID NO: 15) in which Y equals pyrimidines and N equals any base. The C-terminus of ClfA has features present in many surface proteins of gram-positive bacteria such as an LPDTG (SEQ ID NO: 16) motif, which is responsible for anchoring the protein to the cell wall, a membrane anchor, and positive charged residues at the extreme C-terminus.

The platelet integrin alpha IIbβ3 recognizes the C-terminus of the gamma chain of fibrinogen. This is a crucial event in the initiation of blood clotting during coagulation. ClfA and alpha IIbβ3 appear to recognize precisely the same sites on fibrinogen gamma chain because ClfA can block platelet aggregation, and a peptide corresponding to the C-terminus of the gamma chain (198-41 1) can block both the integrin and ClfA interacting with fibrinogen (McDevitt et al., Eur. J. Biochem. 247:416-424 (1997)). The fibrinogen binding site of alpha IIbβ3 is close to, or overlaps, a Ca2+ binding determinant referred to as an "EF hand". ClfA region A carries several EF hand-like motifs. A concentration of Ca2+ in the range of 3-5 mM blocks these ClfA-fibrinogen interactions and changes the secondary structure of the ClfA protein. Mutations affecting the ClfA EF hand reduce or prevent interactions with fibrinogen. Ca2+ and the fibrinogen gamma chain seem to bind to the same, or to overlapping, sites in ClfA region A.

The alpha chain of the leukocyte integrin, alpha MB2, has an insertion of 200 amino acids (A or I domain) which is responsible for ligand binding activities. A novel metal ion-dependent adhesion site (MIDAS) motif in the I domain is required for ligand binding. Among the ligands recognized is fibrinogen. The binding site on fibrinogen is in the gamma chain (residues 190-202). It was recently reported that Candida albicans has a surface protein, alpha Intlp, having properties reminiscent of eukaryotic integrins. The surface protein has amino acid sequence homology with the I domain of M132, including the MIDAS motif. Furthermore, Intlp binds to fibrinogen.

ClfA region A also exhibits some degree of sequence homology with alpha Intlp. Examination of the ClfA region A sequence has revealed a potential MIDAS motif Mutations in putative cation coordinating residues in the DxSxS portion of the MIDAS motif in ClfA results in a significant reduction in fibrinogen binding. A peptide corresponding to the gamma-chain binding site for alpha Mβ2 (190-202) has been shown by O'Connell et al. to inhibit ClfA-fibrinogen interactions (O'Connell, *J. Biol. Chem.*, in press, 1998). Thus it appears that ClfA can bind to the gamma-chain of fibrinogen at two separate sites. The ligand binding sites on ClfA are similar to those employed by eukaryotic integrins and involve divalent cation binding EF-hand and MIDAS motifs.

Also known is the fibrinogen binding protein, ClfB. Used herein are the protein as well as antibodies to the protein and diagnostic kits that include the protein or its antibodies. ClfB has a predicted molecular weight of approximately 88 kDa and an apparent molecular weight of approximately 124 kDa. ClfB is a cell-wall associated protein and binds both soluble and immobilized fibrinogen. In addition, ClfB binds both the alpha and beta chains of fibrinogen and acts as a clumping factor.

Proteins related to the fibrinogen-binding ClfA and ClfB have been found, which bind to the extracellular matrix. The SdrC, SdrD and SdrE proteins are related in primary sequence and structural organization to the ClfA and ClfB proteins, and are also localized on the cell surface. With the A region of these proteins localized on the cell surface, the proteins can interact with the proteins in plasma, the extracellular matrix or with molecules on the surface of host cells. SdrC can bind to the extracellular matrix proteins, for example, vitronectin. SdrE also binds to the extracellular matrix, for example, SdrE binds bone sialoprotein (BSP).

It has been discovered that in the A region of SdrC, SdrD, SdrE, ClfA, and ClfB, there is highly conserved amino acid sequence that can be used to derive a consensus TYTFT-DYVD (SEQ ID NO: 17) motif. The motif can be used in multicomponent vaccines to impart broad spectrum immunity to bacterial infections, and also can be used to produce monoclonal or polyclonal antibodies that impart broad spectrum passive immunity. In an alternative embodiment, any combination of the variable sequence motif derived from the Sdr and Clf protein families, (T/I) (Y/F) (T/V) (F) (T) (D/N) (Y) (V) (D/N), can be used to impart immunity or to induce protective antibodies.

V. ELASTIN-BINDING MSCRAMMs

The primary role of elastin is to confer the property of reversible elasticity to tissues and organs (Rosenbloom, J., et al., *FASEB J.*, 7:1208-1218, 1993). Elastin expression is highest in the lung, skin and blood vessels, but the protein is widely expressed in mammalian hosts for *S. aureus. S. aureus* binding to elastin was found to be rapid, reversible, of high affinity and ligand specific. Furthermore, a 25 kDa cell surface elastin binding protein (EbpS) was isolated and proposed to mediate *S. aureus* binding to elastin-rich host ECM. EbpS binds to a region in the N-terminal 30 kDa fragment of elastin.

PCT/US97/03106 discloses the gene sequences for an elastin binding protein. DNA sequence data disclosed indicates that the ebps open reading frame consists of 606 bp, and encodes a novel polypeptide of 202 amino acids. EbpS protein has a predicted molecular mass of 23,345 daltons and pI of 4.9. EbpS was expressed in *E. coli* as a fusion protein with polyhistidine residues attached to the N-terminus. A polyclonal antibody raised against recombinant EbpS interacted specifically with the 25 kDa cell surface EbpS and inhibited staphylococcal elastin binding. Furthermore, recombinant EbpS bound specifically to immobilized elastin and inhibited binding of *Staphylococcus aureus* to elastin. A degradation product of recombinant EbpS lacking the first 59 amino acids of the molecule and a C-terminal fragment of CNBr-cleaved recombinant EbpS, however, did not interact with elastin. These results strongly suggest that EbpS is the cell surface molecule mediating binding of *Staphylococcus aureus* to elastin. The finding that some constructs of recombinant EbpS do not interact with elastin suggests that the elastin binding site in EbpS is contained in the first 59 amino acids of the molecule.

Several independent criteria indicate that EbpS is the surface protein mediating cellular elastin binding. First, rEbpS binds specifically to immobilized elastin and inhibits binding of *S. aureus* cells to elastin in a dose dependent manner. These results establish that EbpS is an elastin binding protein that is functionally active in a soluble form. Second, an antibody raised against rEbpS recognizes a 25 kDa protein expressed on the cell surface of *S. aureus* cells. In addition to the size similarity and antibody reactivity, further evidence that this 25 kDa protein is cell surface EbpS is provided by the experiment showing that binding of the 25 kDa protein to immobilized anti-rEbpS IgG is inhibited in the presence of excess unlabeled rEbpS. Finally, Fab fragments prepared from the anti-rEbpS antibody, but not from its pre-immune control, inhibit binding of *S. aureus* to elastin. This result suggests that the topology of surface EbpS is such that the elastin binding site is accessible to interact with ligands (i.e. elastin and the anti-rEbpS Fab fragment) and not embedded in the cell wall or membrane domains. The composite data demonstrate that EbpS is the cell surface protein responsible for binding *S. aureus* to elastin.

The present and previous findings suggest the existence of a functionally active 40 kDa intracellular precursor form of EbpS that requires processing at the C terminus prior to surface expression. This notion is based on the following observations: i) there exists an intracellular 40 kDa elastin binding protein that is never detected during cell surface labeling experiments, ii) the 25 kDa EbpS and the 40 kDa elastin binding protein have an identical N-terminal sequence, and iii) a single gene exists for EbpS. Because the size of the ebps open reading frame is not sufficient to encode a 40 kDa protein, at first the inventors disregarded this hypothesis. However, their studies with rEbpS demonstrated that although the actual size of the recombinant protein is 26 kDa, it migrates aberrantly as a 45 kDa protein in SDS-30 PAGE. This finding suggests that full length native EbpS, with a predicted size of 23 kDa, may be migrating in SDS-PAGE as the 40 kDa intracellular precursor, and that the 25 kDa surface form of EbpS is actually a smaller form of the molecule processed at the C-terminus. Although EbpS lacks an N-terminal signal peptide and other known sorting and anchoring signals, this proposed intracellular processing event may explain some questions regarding how EbpS is targeted to the cell surface. In fact, C-terminal signal peptides have been identified in several bacterial proteins (Fath, M. J. and Kolter, R., *Microbiol. Rev.*, 57:995-1017, 1993) and alternative means of anchoring proteins to the cells surface have been reported in gram positive bacteria (Yother, J. and White, J. M., *J. Bacteriol.*, 176:2976-2985, 1994).

Using overlapping EbpS fragments and recombinant constructs, the elastin binding site in EbpS was mapped to the amino terminal domain of the molecule (PCT/US97/03106). Overlapping synthetic peptides spanning amino acids 14-34 were then used to better define the binding domain. Among these, peptides corresponding to residues 14-23 and 18-34 specifically inhibited elastin binding by more than 95%. Common to all active synthetic peptides and proteolytic and recombinant fragments of EbpS is the hexameric sequence $^{18}$Thr-Asn-Ser-His-Gln-Asp$^{23}$ (SEQ ID NO: 18). Further evidence that this sequence is important for elastin binding was the loss of activity when Asp$^{23}$ was substituted with Asn in the synthetic peptide corresponding to residues 18-34. However, the synthetic hexamer TNSHQD (SEQ ID NO: 18) by itself did not inhibit staphylococcal binding to elastin. These findings indicate that although the presence of the TNSHQD sequence is essential for EbpS activity, flanking amino acids in the N- or C-terminal direction and the carboxyl side chain of Asp$^{23}$ are required for elastin recognition.

VI. MHC II-ANALOGOUS PROTEINS, (MAP)

In addition to fibrinogen, fibronectin, collagen and elastin, *S. aureus* strains associate with other adhesive eukaryotic proteins, many of which belong to the family of adhesive matrix proteins, such as vitronectin. (Chatwal et al., *Infect. Immun.*, 55:1878-1883, 1987). U.S. Pat. No. 5,648,240 discloses a DNA segment comprising a gene encoding a *S. aureus* broad spectrum adhesin that has a molecular weight of about 70 kDa. The adhesin is capable of binding fibronectin or vitronectin and includes a MHC II mimicking unit of about 30 amino acids. Further analyses of the binding specificities of this protein reveal that it functionally resembles an MHC II antigen in that it binds synthetic peptides. Thus, in addition to mediating bacterial adhesion to ECM proteins, it may play a role in staphylococcal infections by suppressing the immune system of the host. The patent further claims a recombinant vector that includes the specified DNA sequence, a recombinant host cell transformed with the vector, and DNA which hybridizes with the DNA of specified sequence. Also disclosed is a composition that includes a protein or polypeptide encoded by the specified DNA sequence and a method of inducing an immune response in an animal that includes administering an immunogenic composition that includes the encoded protein or polypeptide. A method of making a MHC II antigen protein analog comprising the steps of inserting the specified DNA sequence in a suitable expression vector and culturing a host cell transformed with the vector under conditions to produce the MHC II antigen protein analog is additionally claimed in the patent.

VII. SDR PROTEINS FROM STAPHYLOCOCCUS EPIDERMIDIS

*Staphylococcus epidermidis*, a coagulase-negative bacterium, is a common inhabitant of human skin and a frequent cause of foreign-body infections. Pathogenesis is facilitated by the ability of the organism to first adhere to, and subsequently to form biofilms on, indwelling medical devices such as artificial valves, orthopedic devices, and intravenous and peritoneal dialysis catheters. Device-related infections may jeopardize the success of medical treatment and significantly increase patient mortality. Accordingly, the ability to develop vaccines that can control or prevent outbreaks of *S. epidermidis* infection is of great importance, as is the development of multicomponent vaccines that can prevent or treat infection from a broad spectrum of bacteria, including both coagulase-positive and coagulase negative bacteria at the same time.

Three Sdr (serine-aspartate (SD) repeat region) proteins that are expressed by *S. epidermidis* have been designated as SdrF, SdrG and SdrH, and the amino acid sequences of these proteins and their nucleic acid sequences are shown in FIGS. 3-5, respectively. In addition, a more complete description of these proteins is provided in a co-pending U.S. patent application of Foster et al. which is based on U.S. provisional application Ser. Nos. 60/098,443 and 60/117,119. These applications are incorporated herein by reference.

In accordance with the present invention, a composition useful as a vaccine is provided that includes the components of any of the above embodiments in combination with an SdrF, SdrG or an SdrH protein. In addition, antibodies to these proteins can be raised using conventional means, and antibodies to the SdrF, SdrG or an SdrH proteins can be employed in any of the above combinations which employ antibodies to the other adhesins discussed herein. The compositions and vaccines which include an SDR protein such as SdrF, SdrG or SdrH can thus be used to treat a broad spectrum of bacterial infections, including those arising both from coagulase-positive and coagulase-negative bacteria.

VIII. BACTERIAL COMPONENTS

In an embodiment of the invention, a composition is provided that includes the components of any of the above embodiments in combination with a bacterial component, preferably capsular polysaccharides type 5 or type 8, to increase the rate of opsonization and phagocytosis of *S. aureus*.

Staphylococci contain antigenic polysaccharides, such as capsular polysaccharide types 5 and 8, and proteins as well as other substances important in cell wall structure. Peptidoglycan, a polysaccharide polymer containing linked subunits, provides the rigid exoskeleton of the cell wall. Peptidoglycan is destroyed by strong acids or exposure to lysozyme. It is important in the pathogenesis of infection. It elicits production of interleukin-1 (endogenous pyrogen) and opsonic antibodies by monocytes. It can be a chemoattractant for polymorphonuclear leukocytes, have endotoxin-like activity, produce a localized Shwartzman phenomenon, and activate complement.

Teichoic acids, lipoteichoic acid for example, which are polymers of glycerol or ribotol phosphate, are linked to the peptidolglycan and can be antigenic. Antiteichoic antibodies detectable by gel diffusion may be found in patients with active endocarditis due to *S. aureus*.

Protein A is a cell wall component of many *S. aureus* strains that binds to the Fc portion of IgG molecules except IgG3. The Fab portion of IgG bound to protein A is free to combine with a specific antigen. Protein A has become an important reagent in immunology and diagnostic laboratory technology; for example, protein A with attached IgG molecules directed against a specific bacterial antigen will agglutinate bacteria that have that antigen ("coagglutination").

Some *S. aureus* strains have capsules, which inhibit phagocytosis by polymorphonuclear leukocytes unless specific antibodies are present. Most strains of *S. aureus* have coagulase, or clumping factor, on the cell wall surface; coagulase binds nonenzymatically to fibrinogen, yielding aggregation of the bacteria.

Staphylococci can produce disease both through their ability to multiply and spread widely in tissues and through their production of many extracellular substances. Some of these substances are enzymes; others are considered to be toxins, though they may function as enzymes. Many of the toxins are under the genetic control of plasmids; some may be under both chromosomal and extrachromosomal control; and for others the mechanism of genetic control is not well defined.

A. Catalase: Staphylococci produce catalase, which converts hydrogen peroxide into water and oxygen. The catalase test differentiates the staphylococci, which are positive, from the streptococci, which are negative.

B. Coagulase: *S. aureus* produces coagulase, an enzyme-like protein that clots oxalated or citrated plasma in the presence of a factor contained in many sera. The serum factor reacts with coagulase to generate both esterase and clotting activities, in a manner similar to the activation of prothrombin to thrombin. The action of coagulase circumvents the normal plasma clotting cascade. Coagulase may deposit fibrin on the surface of staphylococci, perhaps altering their ingestion by phagocytic cells or their destruction within such cells. Coagulase production is considered synonymous with invasive pathogenic potential. However, coagulase-negative bacteria such as S. epidermidis also pose a threat for serious infection as well.

C. Other Enzymes: Other enzymes produced by staphylococci include a hyaluronidase, or spreading factor; a staphylokinase resulting in fibrinolysis but acting much more slowly than streptokinase; proteinases; lipases; and β-lactamase.

D. Exotoxins: These include several toxins that are lethal for animals on injection, cause necrosis in skin, and contain soluble hemolysins which can be separated by electrophoresis. The alpha toxin (hemolysin) is a heterogeneous protein that can lyse erythrocytes and damage platelets and is probably identical with the lethal and dermonecrotic factors of exotoxin. Alpha toxin also has a powerful action on vascular smooth muscle. Beta toxin degrades sphingomyelin and is toxic for many kinds of cells, including human red blood cells. These toxins and two others, the gamma and delta toxins; are antigenically distinct and bear no relationship to streptococcal lysins. Exotoxin treated with formalin gives a non-poisonous but antigenic toxoid, but this is not clinically useful.

E. Leukocidin: This toxin of S. aureus can kill exposed white blood cells of many animals. Its role in pathogenic staphylococci may not kill white blood cells and may be phagocytosed as effectively as nonpathogenic varieties. However, they are capable of very active intra-cellular multiplication, whereas the nonpathogenic organisms tend to die inside the cell. Antibodies to leukocidin may plan a role in resistance to recurrent staphylococcal infections.

F. Exfoliative Toxin: This toxin of S. aureus includes at least two proteins that yield the generalized desquamation of the staphylococcal scaled skin syndrome. Specific antibodies protect against the exfoliative action of the toxin.

G. Toxic Shock Syndrome Toxin. Most S. aureus strains isolated from patients with toxic shock syndrome produce a toxin called toxic shock syndrome toxin-1 (TSST-1), which is the same as enterotoxin F and pyrogenic exotoxin C. TSST-1 is the prototypical superantigen which promotes the protean manifestations of the toxic shock syndrome. In humans, the toxin is associated with fever, shock, and multisystem involvement, including a desquamative skin rash. In rabbits, TSST-1 produces fever, enhanced susceptibility to the effects of bacterial lipopolysaccharides, and other biologic effects similar to toxic shock syndrome, but the skin rash and desquamation do not occur.

H. Enterotoxins: There are at least six (A-F) soluble toxins produced by nearly 50% of S aureus strains. Like TSST-1, the enterotoxins are superantigens that bind to MHC class II molecules, yielding T cell stimulation. The enterotoxins are heat-stable (they resist boiling for 30 minutes) and are resistant to the action of gut enzymes. An important cause of food poisoning, enterotoxins are produced when S. aureus grows in carbohydrate and protein foods. The gene for enterotoxin production may be on the chromosome, but a plasmid may carry a protein that regulates active toxin production. Ingestion of 25 µg of enterotoxin B by humans or monkeys results in vomiting and diarrhea. The emetic effect of enterotoxin is probably the result of central nervous system stimulation (vomiting center) after the toxin acts on neural receptors in the gut. Enterotoxins can be assayed by precipitin tests (gel diffusion).

There are also many other antigenic proteins produced by Staphylococcal organisms. These include the MSCRAMMs mentioned above, as well as: bone sialoprotein binding protein, clusterin binding protein, heparin sulfate binding protein, thrombospondin binding protein, transferrin binding protein and vitronectin binding protein. S. aureus further expresses virulence factors such as phophatidyl phospholipase, and toxin expression regulators such as Rap protein.

IX. PROTEINS AND PEPTIDES WITH SUBSTANTIAL HOMOLOGY OR EQUIVALENT FUNCTION TO THOSE DESCRIBED HEREIN

The disclosed compositions can include, as desired, full sequence proteins, peptides, protein or peptide fragments, isolated epitopes, fusion proteins, or any alternative which binds to the target ECM, whether in the form of a wild type, a site-directed mutant, or a sequence which is substantially homologous thereto.

Two DNA sequences are "substantially homologous" when at least about 70%, (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., *Molecular Cloning: A Laboratory Manual*, 1982; *DNA Cloning*, Vols. I & II, supra; *Nucleic Acid Hybridization*, [B. D. Hames & S. J. Higgins eds. (1985)].

When used in conjunction with amino acid sequences, the term "substantially similar" means an amino acid sequence which is not identical to published sequences, but which produces a protein having the same functionality and activities, either because one amino acid is replaced with another similar amino acid, or because the change (whether it be substitution, deletion or insertion) does not substantially effect the active site of the protein. Two amino acid sequences are "substantially homologous" when at least about 70%, (preferably at least about 80%, and most preferably at least about 90% or 95%) of the amino acids match over the defined length of the sequences.

It should also be understood that each of the MSCRAMM polypeptides of this invention may be part of a larger protein. For example, a ClfA polypeptide of this invention may be fused at its N-terminus or C-terminus to a ClfB polypeptide, or to a non-fibrinogen binding polypeptide or combinations thereof. Polypeptides which may be useful for this purpose include polypeptides derived any of the MSCRAMM proteins, and serotypic variants of any of the above. Non-MSCRAMM polypeptides which may be useful for this purpose include any of the bacterial components described above.

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second generation molecule. The amino acid changes may be achieved by changing the codons of the DNA sequence, according to Table 1. It should be understood by one skilled in the art that the codons specified in Table 1 are for RNA sequences. The corresponding codons for DNA have a T substituted for U. In keeping with standard nomenclature (*J. Biol. Chem.*, 243:3552-3559, 1969), abbreviations for amino acid residues are further shown in Table I.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE I

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | GAC | GAU | |
| Glutamic acid | Glu | E | GAA | GAG | | | |
| Phenylalanine | Phe | F | UUC | UUU | | | |
| Glycine | Gly | G | GGA | GCG | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | GUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, *J Mol Biol*, 157(1):105-132, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, supra 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+1.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The polypeptides of the present invention can be can be chemically synthesized. The synthetic polypeptides are prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149-2154 (1963)], or the base-labile N'-amino protected 9-fluorenylmethoxycarbonyl (Fmoc) amino acids first described by Carpino and Han [*J. Org. Chem.*, 37:3403-3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$—protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields et al., *Int. J. Pept. Protein es.* 35:161-214 (1990), or using automated synthesizers, such as sold by ABS. Thus, polypeptides of the invention may comprise D-amino acids, a combination of D- and L-amino acids, and various "designer" amino acids (e.g., β-methyl amino acids, Ca-methyl amino acids, and Na-methyl amino acids, etc.) to convey special properties. Synthetic amino acids include ornithine for lysine, fluoro-phenylalanine for phenylalanine, and norleucine for leucine or isoleucine. Additionally, by assigning specific amino acids at specific coupling steps, a-helices, β turns, β sheets, β-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, *Life Sciences,* 31:189-199 (1982)); (Hruby et al., *Biochem J.* 268:249-262 (1990)].

The following non-classical amino acids may be incorporated in the peptide in order to introduce particular conformational motifs: 1,2,3,4-tetrahydroisoquinoline-3-carboxylate (Kazmierski et al., *J. Am. Chem. Soc.,* 113:2275-2283, 1991); (2S,3S)-methyl-phenylalanine, (2S,3R)-methyl-phenylalanine, (2R,3 S)-methyl-phenylalanine and (2R,3R)-methyl-phenylalanine (Kazmierski and Hruby, *Tetrahedron Lett.,* 1991); 2-aminotetrahydronaphthalene-2-carboxylic acid (Landis, Ph.D. *Thesis, University of Arizona,* 1989); hydroxy-1,2,3,4-tetrahydroisoquinoline-3-carboxylate (Miyake et al, *J. Takeda Res. Labs.,* 43:53-76, 1989); β-carboline (D and L) (Kazmierski, *Ph. D. Thesis, University of Arizona,* 1988); HIC (histidine isoquinoline carboxylic acid) (Zechel et al, *Int. J. Pep. Protein Res.,* 43, 1991); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., *J. Org. Chem.,* 50:5834-5838 (1985)]; β-sheet inducing analogs [Kemp et al., *Tetrahedron Lett.,* 29:5081-5082 (1988)]; β-turn inducing analogs [Kemp et al., *Tetrahedron Lett.,* 29:5057-5060 (1988)]; alpha-helix inducing analogs [Kemp et al., *Tetrahedron Lett.,* 29:4935-4938 (1988)]; β-turn inducing analogs [Kemp et al., *J. Org. Chem.,* 54:109:115 (1989)]; and analogs provided by the following references: Nagai and Sato, *Tetrahedron Lett.,* 26:647-650 (1985); DiMaio et al., *J. Chem. Soc. Perkin Trans., p.* 1687 (1989); also a Gly-Ala turn analog (Kahn et al., *Tetrahedron Lett.,* 30:2317, 1989); amide bond isostere (Jones et al., *Tetrahedron Lett.,* 29:3853-3856, 1989); tetrazole (Zabrocki et al., *J. Am. Chem. Soc.,* 110:5875-5880, 1988); DTC (Samanen et al., *Int. J. Protein Pep. Res.,* 35:501:509, 1990); and analogs taught in Olson et al., (*J. Am. Chem. Sci.,* 112:323-333, 1990) and Garvey et al., (*J. Org. Chem.,* 56:436, 1990). Conformationally restricted mimetics of beta turns and beta bulges, and peptides containing them, are described in U.S. Pat. No. 5,440,013, issued Aug. 8, 1995 to Kahn.

X. USES FOR MSCRAMM AND ANTIBODY COMPOSITIONS

The protein compositions disclosed herein can be used for the treatment of wounds, for blocking protein receptors or for immunization (vaccination). In the latter case, the body creates specific antibodies, which can protect against invasion by bacterial strains comprising such a cell surface protein, and whereby the antibodies block the adherence of the bacterial strains to a damaged tissue.

The protein composition can be dispersed in a sterile, isotonic saline solution, optionally with the addition of a pharmaceutically acceptable dispersing agent. Different types of adjuvants can further be used to sustain the release in the tissue, and thus expose the peptide for a longer time to the immune defense system of a body.

The proteins, nucleic acid molecules or antibodies are useful for interfering with the initial physical interaction between a pathogen and mammalian host responsible for infection, such as the adhesion of bacteria, particularly gram positive bacteria, to mammalian extracellular matrix proteins on indwelling devices or to extracellular matrix proteins in wounds; to block protein-mediated mammalian cell invasion; to block bacterial adhesion between mammalian extracellular matrix proteins and bacterial proteins that mediate tissue damage; and, to block the normal progression of pathogenesis in infections initiated other than by the implantation of indwelling devices or surgical techniques. Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber, posterior chamber or phasic), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethra/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

The term "coated" or "coating", as used herein, means to apply the protein, antibody, or active fragment to a surface of the device, preferably an outer surface that would be exposed to *S. aureus* infection. The surface of the device need not be entirely covered by the protein, antibody or active fragment.

XI. PREPARATION OF PROTEINS, DNA, AND ANTIBODIES

The skilled reader can employ conventional molecular biology, microbiology, and recombinant DNA techniques to prepare the proteins, peptides, and antibody compositions described herein. Such techniques are explained fully in the literature. See, e.g., Sambrook et al, *Molecular Cloning: A Laboratory Manual* (1989); *Current Protocols in Molecular Biology* Volumes I-III (Ausubel, R. @-I ed., 1994); *Cell Biology: A Laboratory Handbook* Volumes I-III (J. E. Celis, ed., 1994); *Current Protocols in Immunology* Volumes I-III (Coligan, J. E., ed., 1994); *Oligonucleotide Synthesis* (M. J. Gait ed. 1984); *Nucleic Acid Hybridization* (B. D. Hames & S. J. Higgins eds., 1985); *Transcription And Translation* (B. D. Hames & S. J. Higgins, eds., 1984); *Animal Cell Culture* [R. I. Freshney, ed. 1, (1986); *Immobilized Cells And Enzymes* [IRL Press, (1986)]; B. Perbal, *A Practical Guide To Molecular Cloning* (1984).

Reference to antibodies throughout the specification includes whole polyclonal and monoclonal antibodies, and parts thereof, either alone or conjugated with other moieties. Antibody parts include Fab and F(ab)2 fragments and single chain antibodies. The antibodies may be made in vivo in suitable laboratory animals or in vitro using recombinant DNA techniques. An antibody can be a polygonal or a monoclonal antibody. In a preferred embodiment, an antibody is a polyclonal antibody. Means for preparing and characterizing antibodies are well known in the art (See, e.g., Harlow and Lane, *Antibodies: a Laboratory Manual*, Cold Spring Harbor, N.Y., 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for MSCRAMM epitopes may be prepared using conventional immunization techniques, as will be generally known to those of skill in the art. A composition containing antigenic epitopes of particular binding MSCRAMMs (either synthetic peptides, site-specifically mutated, or truncated peptides) can be used to immunize one or more experimental animals, such as a rabbit or mouse, which will then proceed to produce specific antibodies against epitope-containing MSCRAMM peptides.

Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored.

One of the important features provided by the present invention is a polygonal sera that is relatively homogenous with respect to the specificity of the antibodies therein. Typically, polygonal antisera is derived from a variety of different "clones," i.e., B-cells of different lineage. Monoclonal antibodies, by contrast, are defined as coming from antibody-producing cells with a common B-cell ancestor, hence their "mono" clonality.

When peptides are used as antigens to raise polyclonal sera, one expects considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to the present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain monoclonal antibodies, one also initially immunizes an experimental animal, often preferably a mouse, with an MSCRAMM-derived epitope-containing composition. One then, after a period of time sufficient to allow antibody generation, obtains a population of spleen or lymph cells from the animal. The spleen or lymph cells are then fused with cell lines, such as human or mouse myeloma strains, to produce antibody-secreting hybridomas. These hybridomas may be isolated to obtain individual clones which can then be screened for production of antibody to the desired peptide. Following immunization, spleen cells are removed and fused, using a standard fusion protocol with plasmacytoma cells to produce hybridomas secreting monoclonal antibodies against MSCRAMM-derived epitopes. Hybridomas which produce monoclonal antibodies to the selected antigens are identified using standard techniques, such as ELISA and Western blot methods. Hybridoma clones can then be cultured in liquid media and the culture supernatants unified to provide the MSCRAMM-derived epitope-specific monoclonal antibodies.

Immortal antibody-producing cell lines can also be created by techniques other than fusion, such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies And T-cell Hybridomas* (1981); Kennett et al., *Monoclonal Antibodies* (1980); see also U.S. Pat. Nos. 4,341,761; 4,399,121; 4,427,783; 4,444,887; 4,451,570; 4,466,917; 4,472,500; 4,491,632; 4,493,890.

It is proposed that the monoclonal antibodies of the present invention will find useful application in standard immunochemical procedures, such as ELISA and Western blot methods, as well as other procedures which may utilize antibody specific to the MSCRAMM epitopes.

Additionally, it is proposed that monoclonal antibodies specific to the particular MSCRAMM-derived peptides may be utilized in other useful applications. For example, their use in immunoabsorbent protocols may be useful in purifying native or recombinant peptide species or synthetic or natural variants thereof.

In general, both poly- and monoclonal antibodies against these peptides may be used in a variety of embodiments. For example, they may be employed in antibody cloning protocols to obtain cDNAs or genes encoding the peptides discussed herein or related proteins. They may also be used in inhibition studies to analyze the effects of MSCRAMM-derived peptides in cells or animals. Anti-MSCRAMM epitope antibodies will also be useful in immunolocalization studies to analyze the distribution of MSCRAMMs during various cellular events, for example, to determine the cellular or tissue-specific distribution of the MSCRAMM peptides under different physiological conditions. A particularly useful application of such antibodies is in purifying native or recombinant MSCRAMMs, for example, using an antibody affinity column. The operation of all such immunological techniques will be known to those of skill in the art in light of the present disclosure.

Techniques for the production of single chain antibodies are known to those skilled in the art and described in U.S. Pat. No. 4,946,778 and can be used to produce single chain antibodies to the proteins described herein. Phage display technology may be used to select antibody genes having binding, activities for MSCRAMMs, or antigenic portions thereof, from PCR-amplified v genes of lymphocytes from humans screened for having antibodies to MSCRAMMs or naive libraries. Bispecific antibodies have two antigen binding domains wherein each domain is directed against a different epitope.

The antibody may be labeled directly with a detectable label for identification and quantification of a staphylococcal bacterium such as *S. aureus*. Labels for use in immunoassays are generally known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA).

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art. Antibodies to the binding proteins may also be used in production facilities or laboratories to isolate additional quantities of the protein, such as by affinity chromatography.

In general, the preparation of bispecific antibodies is also well known in the art, as exemplified by Glennie et al. (*J Immunol*, 139:2367-2375, 1987). Bispecific antibodies have been employed clinically, for example, to treat cancer patients (Bauer et al, *Vox Sang*, 61:156-157, 1991). One method for the preparation of bispecific antibodies involves the separate preparation of antibodies having specificity for different epitopes of one or more fibronectin binding domains from one or more fibronectin binding protein(s).

While numerous methods are known in the art for the preparation of bispecific antibodies, the Glennie et al., (1987 supra) method involves the preparation of peptic F(ab'Y)$_2$ fragments from the two chosen antibodies, followed by reduction of each to provide separate Fab'YSH fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'Y)2 heteroconjugate.

Due to ease of preparation, high yield and reproducibility, the Glennie et al., (1987 supra) method is often preferred for the preparation of bispecific antibodies, however, there are numerous other approaches that can be employed and that are envisioned by the inventors. For example, other techniques are known wherein cross-linking with SPDP or protein A is carried out, or a specific construct is prepared (Titus et al, *J. Immunol.*, 138:4018-4022, 1987; Tutt et al, *Eur J Immunol*, 21:1351-1358, 1991).

Another method for producing bispecific antibodies is by the fusion of two hybridomas to form a quadroma (Flavell et al, *Br. J. Cancer*, 64(2):274-280, 1991; Pimm et al, *J. Cancer Res Clin Oncol*, 118:367-370, 1992; French et al, *Cancer Res*, 51:2358-2361, 1991; Embleton et al., *Br. J. Cancer*, 63(5): 670-674, 1991). As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen mAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1\times10^7$ M to $1\times10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired MAb is used to generate the quadromas by standard cell fusion techniques (Galfre et al, *Methods Enzymol*, 73:1-46, 1981), or by using the protocol described by Clark et al (*Int J Cancer*, 2:15-17, 1988). Briefly, $4.5\times10^7$ HAT-sensitive first cells are mixed with 2.8× phosphate buffered saline) for 30 in minutes on ice before fusion. Cell fusion is induced using polyethylene glycol (PEG) and the cells are plated out in 96 well microculture plates. Quadromas are selected using Hat-containing medium. Bispecific antibody-containing cultures are identified using, for example, a solid phase isotype-specific ELISA and isotype-specific immunofluorescence staining.

In one identification embodiment to identify the bispecific antibody, the wells of microliter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-anti-antibody conjugate added for 2 hours at room temperature. The plates are washed and a phosphatase substrate, e.g., p-Nitrophenyl phosphate (Sigma, St. Louis) is added to each well. Plates are incubated, 3N NaOH is added to each well to stop the reaction, and the OD410 values determined using an ELISA reader.

In another identification embodiment, microliter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation Procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

Furthermore, recombinant technology is now available for the preparation of antibodies in general, allowing the preparation of recombinant antibody genes encoding an antibody having the desired dual specificity (Van Duk et al., *Int J. Cancer*, 43:344-349, 1989). Thus, after selecting the monoclonal antibodies having the most preferred binding characteristics, the respective genes for these antibodies can be isolated, e.g., by immunological screening of a phage expression library (Oi and Morrison, 1986; Winter and Milstein, 1991). Then, through rearrangement of Fab coding domains, the appropriate chimeric construct can be readily obtained.

Humanized monoclonal antibodies are antibodies of animal origin that have been modified using genetic engineering techniques to replace constant region and/or variable region framework sequences with human sequences, while retaining the original antigen specificity.

Such antibodies are commonly derived from rodent antibodies with specificity against human antigens. Such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarily determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference.

Using the peptide antigens described herein, the present invention also provides methods of generating an immune response, which methods generally comprise administering to an animal, a pharmaceutically-acceptable composition comprising an immunologically effective amount of an MSCRAMM-derived peptide composition. Preferred animals include mammals, and particularly humans. Other preferred animals include murines, bovines, equines, porcines, canines, and felines. The composition may include partially or significantly purified MSCRAMM-derived peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 30 and about 100 amino acids in length will often be preferred. The antigenic proteins or peptides may also be combined with other agents, such as other staphylococcal or streptococcal peptide or nucleic acid compositions, if desired. The composition may also include staphylococcal produced bacterial components such as those discussed above, obtained from natural or recombinant sources, which proteins may be obtainable naturally or either chemically synthesized, or alternatively produced in vitro from recombinant host cells expressing DNA segments encoding such peptides.

Immunoformulations of this invention, whether intended for vaccination, treatment, or for the generation of antibodies useful in the detection of staphylococci and streptococci, or prevention of bacterial adhesion to ECM components such as fibronectin, collagen, elastin, fibrinogen or vitronectin may comprise site-specifically mutated, truncated, or synthetically-derived antigenic peptide fragments from these proteins. As such, antigenic functional equivalents of the proteins and peptides described herein also fall within the scope of the present invention.

Further means contemplated by the inventors for generating an immune response in an animal includes administering to the animal, or human subject, a pharmaceutically-acceptable composition comprising an immunologically effective amount of a nucleic acid composition encoding a peptide epitope, or an immunologically effective amount of an attenuated live organism that includes and expresses such a nucleic acid composition.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, effective dose ranges of about 1 ng to 5 mg, 100 ng to 2.5 mg, 1 µg to 750 µg, and preferably about 10 µg to 300 µg of DNA is administered directly into muscle tissue. Subcutaneous injection, intradermal introduction, impression through the skin, and other modes of administration such as intraperitoneal, intravenous, or inhalation delivery are also suitable. It is also contemplated that booster vaccinations may be provided. Following vaccination with an MSCRAMM polynucleotide immunogen, boosting with MSCRAMM protein immunogens such as the M55 gene product is also contemplated.

The polynucleotide may be "naked", that is, unassociated with any proteins, adjuvants or other agents which affect the recipients' immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

In another embodiment, the invention is a polynucleotide which comprises contiguous nucleic acid sequences capable of being expressed to produce a gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an MSCRAMM immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to insure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a CD8+ response to NP that protected mice against challenge with heterologous strains of flu. (Montgomery, D. L. et al., *Cell Mol Biol*, 43(3):285-292, 1997; Ulmer, J. et al., *Vaccine*, 15(8):792-794, 1997)

Cell-mediated immunity is important in controlling infection. Since DNA immunization can evoke both humoral and cell-mediated immune responses, its greatest advantage may be that it provides a relatively simple method to survey a large number of *S. aureus* genes for their vaccine potential.

Immunization by DNA injection also allows the ready assembly of multicomponent subunit vaccines. Simultaneous immunization with multiple influenza genes has recently been reported. (Donnelly, J. et al., *Vaccines,* 55-59, 1994). The inclusion in a *S. aureus* vaccine of genes whose products activate varied and multiple responses from the immune system may also provide thorough protection from subsequent challenge.

Further provided is a composition comprising an isolated nucleic acid segment that encodes a peptide of a binding domain of a binding protein, wherein the peptide does or does not specifically bind to its ligand. It is also contemplated that attenuated organisms may be engineered to express recombinant MSCRAMM gene products and themselves be delivery vehicles for the invention. Particularly preferred are attenuated bacterial species such as *Mycobacterium*, and in particular *M bovis, M smegmatis*, or BCG. Alternatively, pox-, polio-, adeno-, or other viruses, and bacteria such as *Salmonella, Shigella, Listeria, Streptococcus* species may also be used in conjunction with the methods and compositions disclosed herein.

The naked DNA technology, often referred to as genetic immunization, has been shown to be suitable for protection against infectious organisms. Such DNA segments could be used in a variety of forms including naked DNA and plasmid DNA, and may administered to the subject in a variety of ways including parenteral, mucosal, and so-called microprojectile-based "gene-gun" inoculations. The use of nucleic acid compositions of the present invention in such immunization techniques is thus proposed to be useful as a vaccination strategy against at least streptococcal and staphylococcal infection.

It is recognized by those skilled in the art that an optimal dosing schedule of a DNA vaccination regimen may include as many as five to six, but preferably three to five, or even more preferably one to three administrations of the immunizing entity given at intervals of as few as two to four weeks, to as long as five to ten years, or occasionally at even longer intervals.

Particular aspects of the invention concern the use of plasmid vectors for the cloning and expression of recombinant peptides, and particular peptide epitopes comprising either native, or site-specifically mutated binding site epitopes. The generation of recombinant vectors, transformation of host cells, and expression of recombinant proteins is well-known to those of skill in the art. Prokaryotic hosts are preferred for expression of the peptide compositions of the present invention. An example of a preferred prokaryotic host is *E. coli*, and in particular, *E. coli* strains ATCC 69791, BL21(DE3), JMIOI, XL1-Blue™, RRI, LE392, B, $\chi^{776}$ (ATCC 31537), and W3110 (F, λ, prototrophic, ATCC 273325). Alternatively, other Enterobacteriaceae species such as *Salmonella typhimurium* and *Serratia marcescens*, or even other Gram-negative hosts including various *Pseudomonas* species may be used in the recombinant expression of the genetic constructs discussed herein. Additional hosts may include well known eukaryotic and prokaryotic hosts, such as strains of *Bacillus, Streptomyces*, fungi such as yeasts, and animal cells, such as CHO, R1. 1, B-W and L-M cells, African Green Monkey kidney cells (e.g., COS 1, COS 7, BSC1, BSC40, and BMT10), insect cells (e.g., Sf9), and human cells and plant cells in tissue culture.

A wide variety of host/expression vector combinations may be employed in expressing the DNA. Useful expression vectors, for example, may consist of segments of chromosomal, non-chromosomal and synthetic DNA sequences. Suitable vectors include derivatives of SV40 and known bacterial plasmids. e.g., *E. coli* plasmids col El, pCR1, pBR322, pMB9 and their derivatives, plasmids such as RP4; phage DNAs, e.g., the numerous derivatives of phage λ, e.g., NM989, and other phage DNA, e.g., Ml3 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phospho-glycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly with regard to potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences encoding the components of this invention on fermentation or in large scale animal culture.

In certain embodiments, it is also contemplated that the nucleic acid segments discussed herein will be used to transect appropriate host cells. Technology for introduction of DNA into cells is well-known to those of skill in the art. Four general methods for delivering a nucleic segment into cells have been described: (I) chemical methods (Graham and VanDerEb, *Virology,* 54 (2):536-539, 1973); physical methods such as microinjection (Capecchi, *Cell,* 22(2):479-488, 1980), electroporation (Wong and Neuman, *Biochim Biophys Res Commun,* 107(2):584-587, 1982; Fromm et al., *Proc Natl Acad Sci USA,* 82(17):5824-5828, 1985) and the gene gun (Yang et al., *Proc Natl Acad Sci USA,* 87:4144-4148, 1990); (3) viral vectors (Eglitis and Anderson, *Bio/techniques,* 6(7): 608-614, 1988); and (4) receptor-mediated mechanisms (Wagner, et al., *Proc Natl Acad Sci USA,* 89(13):6099-6103, 1992).

DNA sequences encoding MSCRAMM can be prepared synthetically or cloned. The DNA sequence can be designed with the appropriate codons for the MSCRAMM amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express MSCRAMM analogs. Alternatively, DNA encoding analogs can be made by site-directed mutagenesis of native MSCRAMM genes or cDNAs, and analogs can be made directly using conventional polypeptide synthesis. A general method for site-specific incorporation of unnatural amino acids into proteins is described in Noren et al., *Science.* 244:182-188 (April 1989). This method may be used to create analogs with unnatural amino acids.

XII. ANTISENSE OLIGONUCLEOTIDES AND RIBOZYMES

The present invention extends to the preparation of antisense oligonucleotides and ribozymes that may be used to interfere with the expression of the MSCRAMM at the translational level. This approach utilizes antisense nucleic acid and ribozymes to block translation of a specific mRNA, either by masking the mRNA with an antisense nucleic acid or cleaving it with a ribozyme.

Antisense nucleic acids are DNA or RNA molecules that are complementary to at least a portion of a specific mRNA molecule. In the cell, they hybridize to that specific mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into MSCRAMM-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, *Nature,* 334(6183):585-591, 1988) Tetrahymena-type ribozymes recognize four-base sequences, while "hammerhead"-type recognizes eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for MSCRAMM and their ligands.

XIII. PHARMACEUTICAL COMPOSITIONS

A pharmaceutical composition is provided that comprises the binding proteins, the peptides, the antibodies, or the nucleic acids as described above optionally in combination with bacterial components, in a pharmaceutically acceptable excipient, in an effective amount to treat *S. aureus* infection. The compositions are typically used in the preparation of an immunization formulation that optionally includes an adjuvant and other customary additives. The compositions can also comprise diagnostic kits as described herein.

Methods for preparing pharmaceutical compositions which contain polypeptides, analogs or active fragments as active ingredients are well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of MSCRAMM binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the MSCRAMM/MSCRAMM antagonist or analog thereof, and one or more of the following active ingredients: an antibiotic, a steroid.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjutants that enhance the effectiveness of the vaccines.

The preparation of such compositions that are essentially free from endotoxin can be achieved by following the published methodology, for example, U.S. Pat. No. 4,271,147 (incorporated herein by reference) discloses methods for the preparation of *Neisseria meningitides* membrane proteins for use in vaccines.

The immunological compositions, such as vaccines, and other pharmaceutical compositions can be used alone or in combination with other blocking agents to protect against human and animal infections caused by staphylococcal bacteria such as *S. aureus*. In particular, the compositions can be used to protect humans against endocarditis or to protect humans or ruminants against mastitis caused by staphylococcal infections. The vaccine can also be used to protect canine and equine animals against similar staphylococcal infections.

To enhance immunogenicity, the proteins may be conjugated to a carrier molecule.

Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 daltons, preferably greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The MSCRAMM protein or proteins may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. (*J. Immunol.* 147:410-415, 1991) and incorporated by reference herein, encapsulation of the conjugate within a proteoliposome as described by Miller et al., (*J. Exp. Med.* 176:1739-1744, 1992) and incorporated by reference herein, and encapsulation of the protein in lipid vesicles such as Novasome™ lipid vesicles (Micro Vescular Systems, Inc., Nashua, N.H.) may also be useful.

In certain embodiments, the inventors contemplate the use of liposomes and/or nanocapsules for the introduction of particular peptides or nucleic acid segments into host cells. In particular, the malonyltyrosyl and phosphotyrosyl peptides of the present invention may be formulated for delivery in solution with DMSO or encapsulated in liposomes.

Such formulations may be preferred for the introduction of pharmaceutically acceptable formulations of the nucleic acids, peptides, and/or antibodies disclosed herein. The formation and use of liposomes is generally known to those of skill in the art (see for example, Couvreur et al, *FEBS Lett*, 84:323-326, 1977; and *Crit Rev Ther Drug Carrier Syst*, 5:1-20, 1988 which describes the use of liposomes and nanocapsules in the targeted antibiotic therapy of intracellular bacterial infections and diseases). Recently, liposomes were developed with improved serum stability and circulation half-times (Gabizon and Papahadjopoulos, *Proc Natl Acad Sci USA*, 85:6949-6953, 1988; Allen and Choun, *FEBS Lett*, 223:42-46, 1987).

Liposomes have been used successfully with a number of cell types that are normally resistant to transfection by other procedures including T cell suspensions, primary hepatocyte cultures and PC 12 cells (Muller et al., *DNA Cell Biol*, 9(3): 221-229, 1990). In addition, liposomes are free of the DNA length constraints that are typical of viral-based delivery systems. Liposomes have been used effectively to introduce genes, drugs, radiotherapeutic agents, enzymes, viruses, transcription factors and allosteric effectors into a variety of cultured cell lines and animals. In addition, several successful clinical trails examining the effectiveness of liposome-mediated drug delivery have been completed (Lopez-Berestein et al, *Cancer Drug Review*, 2(3):183-189, 1985; Sculier et al, *Eur J Cancer Clin Oncol*, 24(3):527-538, 1988). Furthermore, several studies suggest that the use of liposomes is not associated with autoimmune responses, toxicity or gonadal localization after systemic delivery (Mori and Fukatsu, *Epilepsia*, 33(6):994-1000, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 micron. Sonication of MLVs results in the formation of small unilamellar vesicles (SUVS) with diameters in the range of 200 to 500 A, containing an aqueous solution in the core.

Liposomes bear many resemblances to cellular membranes and are contemplated for use in connection with the present invention as carriers for the peptide compositions. They are widely suitable, as both water- and lipid-soluble substances can be entrapped, i.e., in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (*FEBS Lett*, 84:323-326, 1977; and *Crit Rev Ther Drug Carrier Syst*, 5:1-20, 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome C bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVS.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depends on their physical properties, such as size, fluidity and surface charge. They may persist in tissues for hours or days, depending on their composition, and half lives in the blood range from minutes to several hours. Larger liposomes, such as MLVs and LUVS, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the peptides of the present invention. Nanocapsules can generally entrap compounds in a stable and reproducible way (Henry-Michelland et al, *Int J Pharm,* 35:121-127, 1987). To avoid side effects due to intracellular polymeric overloading, such ultrafine particles (sized around 0.1 micron) should be designed using polymers able to be degraded in vivo. Biodegradable poly-alkyl-cyanoacrylate nanoparticles that meet these requirements are contemplated for use in the present invention, and such particles may be easily made, as described by Couvreur et al, (supra, 1977 and 1988).

Suitable methods of administration include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

The carrier to which the protein may be conjugated may also be a polymeric delayed release system. Synthetic polymers are particularly useful in the formulation of a vaccine to effect the controlled release of antigens. For example, the polymerization of methyl methacrylate into spheres having diameters less than one micron has been reported by Kreuter, J., *Microcapsules And Nanoparticles In Medicine And Pharmacology*, M. Donbrow (Ed). CRC Press, p. 125-148.

Microencapsulation of the protein will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide) (PLGA) and other biodegradable polymers. The use of PLGA for the controlled release of antigen is reviewed by Eldridge, J. H., et al. *Current Topics In Microbiology And Immunology,* 146:59-66 (1989).

The preferred dose for human administration is from 0.01 mg/kg to 10 mg/kg, preferably approximately 1 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S) mercury sodium salt) (Sigma Chemical Company, St. Louis, Mo.) or physiologically acceptable preservatives.

It will be readily apparent to one skilled in the art that various substitutions and modifications may be made to the invention disclosed herein without departing from the scope and spirit of the invention.

XIV. KITS

This invention also includes a kit comprising anti-MSCRAMM antibody or an MSCRAMM antigen for the detection and diagnosis of infections caused or exacerbated by *Staphylococcus* bacteria such as *S. aureus* or *S. epidermidis*. The preferred kit contains sufficient antibody to bind substantially all of the antigen in the sample in about ten minutes or less, or sufficient antigen to bind antibodies for MSCRAMMs. The antibody or antigen can be immobilized on a solid support, and can be labeled with a detectable agent, as described above. The kit optionally contains a means for detecting the detectable agent. If the antibody or antigen is labeled with a fluorochrome or radioactive label, no means for detecting the agent will typically be provided, as the user will be expected to have the appropriate spectrophotometer, scintillation counter, or microscope. If the detectable agent is an enzyme, a means for detecting the detectable agent can be supplied with the kit, and would typically include a substrate for the enzyme in sufficient quantity to detect all of the antigen-antibody complex. One preferred means for detecting a detectable agent is a substrate that is converted by an enzyme into a colored product. A common example is the use of the enzyme horseradish peroxidase with 2,2'-azino-di-[3-ethyl-benzothiazoline sulfonate] (ABTS).

The kit can optionally contain a lysing agent that lyses cells present in the sample of body fluid. Suitable lysing agents include surfactants such as Tween-80, Nonidet P40, and Triton X-100. Preferably, the lysing agent is immobilized onto the solid support along with the antibody.

The kit can also contain a buffer solution for washing the substrate between steps. The buffer solution is typically a physiological solution such as a phosphate buffer, physiological saline, citrate buffer, or Tris buffer.

The kit can optionally include different concentrations of a preformed antigen to calibrate the assay. The kit can additionally contain a visual or numeric representation of amounts of antigen in a calibrated standard assay for reference purposes. For example, if an assay is used that produces a colored product, a sheet can be included that provides a depiction of increasing intensities associated with differing amounts of antigen.

The kit can optionally include two antibodies in the detection system. The first antibody which is present in small amounts is specific for the antigen being assayed for. The second antibody provided in higher amounts is used to detect the first antibody. For example, a rabbit antibody can be used to detect the LOOH/amine antigen, and then an anti-rabbit IgG antibody can be used to detect the bound rabbit antibody. Goat antibodies and anti-antibodies are also commonly used.

As one nonlimiting example, a kit for the detection of the lipid peroxidation state of a patient is provided that includes a rabbit antibody specific for desired antibody, anti-rabbit IgG antibody in sufficient amounts to detect the bound first antibody, an enzyme conjugated to the second antibody and a substrate for the enzyme which changes color on exposure to the enzyme. In addition, a kit may be prepared using one or more MSCRAMM antigens such as the M55 domain of the collagen binding protein and the ClfA fibrinogen binding protein, and this kit will enable the detection of samples with antibodies to collagen binding and fibrinogen binding MSCRAMMs.

EXAMPLES

The following examples are included to demonstrate preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing form the spirit and scope of the invention.

Example 1

Preparation of Prototype Four Component MSCRAMM Vaccine

A series of recombinant proteins, representing domains from the collagen, Fn, and Fbg-binding MSCRAMMs (FIG. 1), were overexpressed in *E. coli* and affinity purified by metal chelating chromatography as previously described (see, e.g., Joh et al., *Biochemistry.* 33 (20):6086-6092, 1994; Patti et al., *J. Biol. Chem.* 270, 12005-12011, 1995; McDevitt et al., *Mol. Micro.* 11 (2):237-248, 1994; Ni Eidhin et al., *Infect. Immun. Submitted,* 1998). Used were the following: amino acids contained in the recombinant collagen-binding MSCRAMM expressed from cna (M55, such as disclosed in co-pending U.S. patent application Ser. No. 08/856,253, incorporated herein by reference); amino acids contained in the recombinant fibrinogen-binding MSCRAMM expressed from clfA (pCF40, such as disclosed in U.S. patent application Ser. No. 08/293,728, incorporated herein by reference); amino acids contained in the recombinant fibrinogen-binding MSCRAMM expressed from clfB (Region A, such as disclosed in U.S. application Ser. No. 09/200,650, incorporated herein by reference); and amino acids contained in the recombinant fibronectin-binding MSCRAMM (DUD4, such as those disclosed in co-pending U.S. application Ser. No. 09/010,317, incorporated herein by reference). The recombinant FN-binding MSCRAMM protein DUD4 was treated with formalin (5% formalin overnight, 4° C.) prior to combining it with the M55, Region A from ClfA, and Region A from ClfB.

Example 2

Example of Growing *E. coli* Strains for Production of Recombinant Proteins

Overnight cultures of *E. coli* JM101 or TOP 3 cells (Stratagene) harboring the recombinant plasmids were diluted 1:50 in 1 L of Luria Broth (Gibco BRL) containing 50 mg/mL ampicillin. *E. coli* cells were grown until the culture reached an $OD_{600}$ of 0.5-0.8. Expression of the recombinant proteins was induced by adding IPTG to a final concentration of 0.2 mM. After a three hour induction period, cells were collected by centrifugation, resuspended in 15 mL of Buffer A (5 mM imidazole, 0.5 M NaCl, 20 mM Tris-HCl, pH 7.9) and lysed by passage through a French press twice at 20,000 lb./in². Cell debris was removed by centrifugation at 50,000×g for 10 min and the supernatant was passed through a 0.45 µM filter.

Example 3

Purification of $HIS_6$ Containing Recombinant Proteins Expressed from pQE-30 (Qiagen®: Qiagen Inc. Chatsworth. CA) or PV-4 Based Recombinant Plasmids The recombinant proteins were purified by immobilized metal chelate chromatography, using a column of iminodiacetic acid/Sepharose® 6B Fast Flow (Sigma, St. Louis, Mo.) charged with $Ni^{2+}$; (Porath et al. 1975; Hochuli et al. 1988). The $HIS_6$ tagged proteins were purified by immobilized metal chelate affinity chromatography. More specifically, a column containing iminodiacetic acid Sepharose® 6B FF, connected to a FPLC® system (Pharmacia), was charged with 150 mM $Ni^{++}$ and equilibrated with buffer A (5 mM imidazole, 0.5 M NaCl, 20 mM Tris, pH 7.9). After equilibration, the bacterial supernatant was applied to the column and the column was washed with 10 bed volumes of buffer A. Subsequently, the column was eluted with buffer B (200 mM imidazole, 0.5 M NaCl, 20 mM Tris, pH 7.9). The eluate was monitored for protein by the absorbance at 280 nm and peak fractions were analyzed by SDS-PAGE. Endotoxin was removed from the purified recombinant proteins by detergent extraction with 1% Triton X-114 followed by metal chelate affinity chromatography and passage through a polymyxcin B-sepharose column. The level of endotoxin was quantitated using a chromogenic *Limulus Amebocyte* Lysate (BioWhittaker, Walkersville, Md.) assay.

Example 4

Immunization of Animals with Four Component MSCRAMM Vaccine

MSCRAMM IV Rhesus Monkeys

100 µg of M55 (1 EU/mg), ClfA (2.5 EU/mg), ClfB (<1.0 EU/mg), and DUD4 (<10 EU/mg) were mixed together to form the MSCRAMM IV vaccine. The cocktail was mixed with TiterMax™ Gold (CytRX, Norcross, Ga.) in a 1:1 ratio. Two female rhesus monkeys, ID #495Z & 664U (~9.4 kg), were vaccinated intramuscularly (IM) in the hind quadricep with 200 μl of the vaccine. Twenty-eight days later the two monkeys were boosted IM with 200 μl of the same vaccine formulation. Two additional female monkeys, ID #215W & 203U (~8.0 kg), were immunized with the MSCRAMM IV that was compounded in a 1:1 ratio with aluminum hydroxide (2% Alhydrogel; Superfos, Denmark). Twenty-eight days later the two monkeys were boosted IM with 200 μl of the same vaccine formulation. The clinical regimen followed is described below.

| | |
|---|---|
| Day 0 | 15 ml pre-immunization plasma sample, complete blood chemistry |
| Day 1 | Vaccinate IM hind quadricep with 0.2 ml MSCRAMM IV (100 μg), injection site exam, temperature recorded |
| Day 7 | Liver panel, temperature recorded, injection site exam |
| Day 14 | 15 ml plasma sample |
| Day 21 | 15 ml plasma sample |
| Day 28 | Complete blood chemistry, temperature recorded 15 ml plasma sample, boost with IM injection of 0.2 ml MSCRAMM IV (100 μg) |
| Day 30 | Liver panel, temperature recorded, injection site exam |
| Day 35 | Liver panel, temperature recorded, injection site, 15 ml plasma sample |
| Day 42 | 15 ml plasma sample |
| Day 49 | 15 ml plasma sample |
| Day 106 | 15 ml plasma sample |

All 4 animals seroconverted following the initial immunization. Antibody levels >3 times above background could be detected by ELISA 106 days after the primary vaccination. The four animals received another booster immunization in the 21$^{st}$ week of the study. Each animal was given a booster of four subcutaneous injections of 125 μl of the vaccine for a total booster of 600 μl of the vaccine. Antibody levels at least 3 times above background, and as much as 15 times above background, could be detected by ELISA 189 days after the primary vaccination. See FIG. 2. No adverse injection site reactions were detected by direct observation by veterinarians. In addition, liver enzyme profiles, CBC, and hematology profiles were within the normal range for rhesus monkeys.

Example 5

Analysis of Plasma Samples from the Vaccinated Monkeys were Analyzed by ELISA

Figure 2:
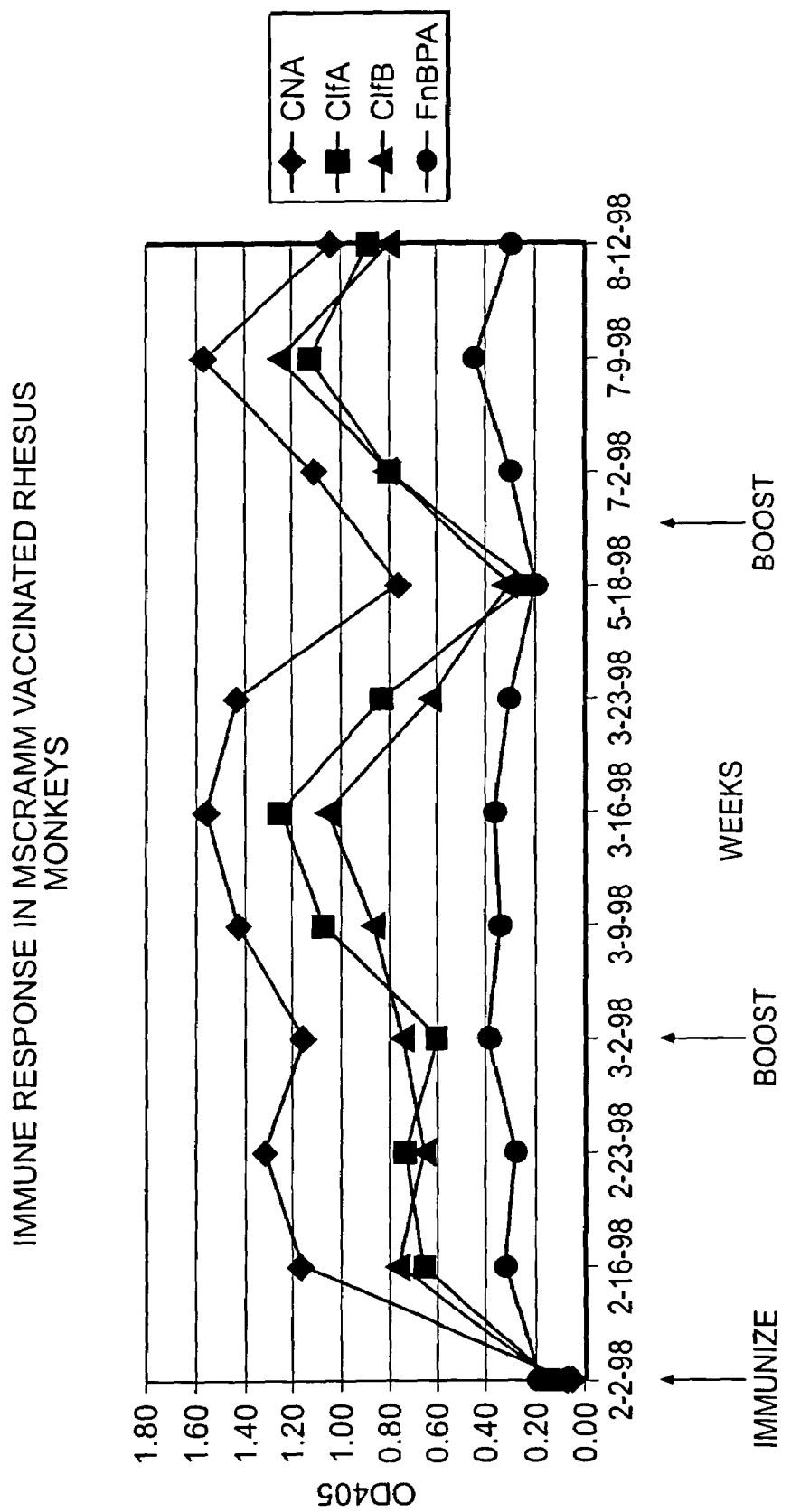

Immulon-2 microtiter plates (Dynex Technologies, Chantilly, Va.) were coated overnight at 4° C. with 10 μg/ml (50 μl) of the collagen binding MSCRAMM (M55), fibrinogen binding MSCRAMM (clfA; pCF44), fibrinogen binding MSCRAMM (ClfB; Region A), and the fibronectin binding MSCRAMM (DUD4). Fifty microliters of the diluted plasma samples were added to the MSCRAMM coated wells and incubated for 1 hr at room temperature. Wash buffer consisting of PBS containing 0.05% vol/vol Tween-20, a blocking solution of 1% wt/vol BSA, 0.05% Tween-20 in PBS, and antibody dilution buffer consisting of PBS containing 0.1% BSA, 0.05% Tween-20. Incubation with primary and secondary antibodies was for 60 min at 25° C. The secondary antibody was alkaline phosphatase-conjugated goat anti-monkey immunoglobulin G, (Rockland, Gilbertsville, Pa.), diluted 3500-fold in antibody dilution buffer. ELISA plates were developed for 30 min at 37° C. with 1 mg/ml p-nitrophenyl phosphate (Sigma) in 1 M diethanolamine, 0.5 mM $MgCl_2$, pH 9.8, and quantified at 405 nm on a Perkin Elmer HTS 7000 Bio-Assay reader. Each plasma sample was diluted 100-fold in phosphate buffered saline, containing 0.05% Tween 20, 0.1% BSA, pH 7.4. ELISA data are shown in FIG. 2.

Example 6

Inhibition Assays

Methicillin resistant *S. aureus* strain 601 (Smeltzer, M. S., *Gene*. 196:249-159, 1997) was cultured under constant rotation for 15 h at 37° C. in BHI broth. A 1:100 dilution of the overnight culture was made into BHI and the bacteria were grown at 37° C. until mid exponential phase. The bacteria were harvested by centrifugation, washed three times in sterile PBS, pH 7.4, and then resuspended in a carbonate buffer (50 mM $NaHCO_3$, pH 8.5). The bacteria were mixed with 1 mg/ml FITC (Sigma; F-7250) in 50 mM $NaHCO_3$, pH 8.5 and incubated end-over-end in the dark for 1 hr at 25° C. The FITC labeling reaction was stopped by centrifugation of the bacterial cells and removing the supernatant containing the unreacted FITC. The labeled bacteria were washed three times in PBS to remove unincorporated FITC, resuspended in PBS, adjusted to ~$1 \times 10^8$ cfu/ml and stored at −20° C. in PBS, pH 7.4.

Example 7

Purification of IgG from Immunized Monkeys

IgG was purified from the monkey plasma by affinity chromatography on PROSEP®-A high capacity resin (Bioprocessing Inc., Princeton, N.J.). Briefly, the plasma was thawed and passed through 0.45% filter. The plasma was applied to a benchtop column containing PROSEP®-A high capacity resin. The unbound material was removed by washing the column extensively with PBS. The IgG was eluted from the column with 0.1 M sodium citrate, pH 3.0. The pH of eluted IgG was immediately neutralized to pH 6.8-7.4 by the addition of 1M Tris, pH 9.0. The IgG was then dialyzed into PBS, pH 7.4, concentrated and filter sterilized. The concentration of the purified IgG was determined by absorbance at 280 nm.

Example 8

Competitive Inhibition ELISA

Costar 96 well black plates were coated overnight at 4° C. or at room temperature for 2 hr with a 10 μg/ml solution of matrix components consisting of bovine collagen, human fibrinogen, and bovine fibronectin in PBS, pH 7.4. The matrix protein coated plates were washed three times with PBS, 0.05% Tween 20 and then blocked with PBS, 1% BSA. The blocked plates were washed three times with PBS, 0.05% Tween 20. A 500 μl aliquot of FITC-labeled *S. aureus* cells were mixed with an increasing amount of purified monkey IgG in PBS, 0.05% Tween 20, 0.1% BSA. The labeled cells and IgG were mixed on an end-over-end shaker for 1 hr at 25° C. Fifty μl of the labeled cells/IgG mixture was added to each well on the microtiter plate and incubated at 25° C. on a rocker platform. The wells were washed three times with PBS, 0.05% Tween 20. The amount of bacteria bound to the immobilized matrix proteins was determined on a Perkin Elmer HTS 7000 Bio-Assay reader with the excitation filter set at 485 nm and the emission filter set at 535 nm.

Example 9

Animal Model of Sepsis

Using a mouse model of sepsis (Bremell, T. A., et al., *Infect. Immun.* 62 (7):2976-2985, 1992) we have demonstrated that passive immunization with IgG purified from rhesus monkeys immunized with the MSCRAMM IV can protect mice against sepsis induced death. Naive male NMRI mice 5-8 weeks old were passively immunized i.p. on day −1 with 20 mg of either purified IgG from rhesus monkeys immunized with MSCRAMM IV (n=12), or IgG from non-immunized rhesus monkeys (n=13). On day 0, the mice were challenged i.v. with $2.4 \times 10^7$ CFU/mouse *S. aureus* strain LS-1. Mortality and weight change was monitored over the next 3 days. Three days after the inoculation 3/13 mice (13%) were dead in the control group, compared to 0/12 mice (0%) in the control group. Mortality in control group at day 13 was 53.8% (7/13) compared to only 16.2% (2/12) for the MSCRAMM IV passively immunized group. The control mice exhibited a significant decrease in their body weight compared to MSCRAMM IV IgG passively immunized mice ($28.0 \pm 2.5\%$ vs $21.3 \pm 3.1\%$; $p<0.01$).

Example 10

Multicomponent Vaccines Containing M55 (Collagen-Binding MSCRAMM) and ClfA (Fibrinogen-Binding MSCRAMM)

Sixty female Swiss Webster mice received a total of 50 μg of either ovalbumin, M55 (collagen-binding MSCRAMM) or a combination of M55 and ClfA (fibrinogen-binding MSCRAMM) proteins via a subcutaneous injection. The primary injection was prepared by emulsifying the antigens in Freund's Complete Adjuvant. The mice received a second injection of 25 μg total protein in Freund's Incomplete Adjuvant 14 days after the primary injection. A final injection of 25 μg total protein in PBS was given 28 days after the primary injection. Post bleed samples from all mice were obtained two weeks after the final injection to determine antibody titers against the different MSCRAMM proteins. The mice were then challenged (42 days after primary injection) via a single intravenous injection with $1.2 \times 10^8$ CFU of *S. aureus* 601. At day 5 post-challenge, the mice were sacrificed and their kidneys harvested. The kidneys were then homogenized and plated on blood agar plates. The plates were incubated at 37° C. overnight and the bacterial load in the kidneys was determined by colony counts. The results of the experiment showed a two log difference in bacterial load between the ovalbumin group ($7.03 \pm 0.93$ log CFU/g) and the M55/ClfA group ($4.83 \pm 3.04$ log CFU/g, $p=0.006$). A difference in bacterial load was also observed in the M55 group ($5.86 \pm 3.42$ log CFU/g, $p=0.003$) when compared to the ovalbumin group.

As shown in the above specification and examples, immunological compositions, including vaccines, and other pharmaceutical compositions containing the MSCRAMM proteins are included within the scope of the present invention. One or more of the binding proteins, or active or antigenic fragments thereof, or fusion proteins thereof can be formulated and packaged, alone or in combination with other antigens, using methods and materials known to those skilled in the art for vaccines. The immunological response may be used therapeutically or prophylactically and may provide antibody immunity or cellular immunity such as that produced by T lymphocytes such as cytotoxic T lymphocytes or CD4+ T lymphocytes.

What is claimed is:

1. A method of generating an immune response, comprising administering to a host an immunologically effective amount of an isolated fibrinogen binding domain of the clumping factor A protein (ClfA) from *Staphylococcus aureus* and an immunologically effective amount of an isolated *S. aureus* capsular polysaccharide type 5.

2. A method of generating an immune response, comprising administering to a host an immunologically effective amount of the A domain of an isolated clumping factor A protein (ClfA) from *Staphylococcus aureus* and an isolated *Staphylococcus aureus* capsular polysaccharide type 5.

3. The method of claim 1 wherein the *S. aureus* capsular polysaccharide type 5 can raise antibodies that can promote bacterial phagocytosis.

\* \* \* \* \*

UNITED STATES PATENT AND TRADEMARK OFFICE
CERTIFICATE OF CORRECTION

PATENT NO. : 7,666,438 B1
APPLICATION NO. : 10/795267
DATED : February 23, 2010
INVENTOR(S) : Patti et al.

It is certified that error appears in the above-identified patent and that said Letters Patent is hereby corrected as shown below:

On the Title page at the field (73) Assignee, please change --Inhibitex, Inc., Alpharetta, GA (US); The Provost Fellows and Scholars of the College of the Holy and Undivived Trinity of Queen Elizabeth Near Dublin, Dublin (IE); The Texas A&M University System, College Station, TX (US)-- to "Inhibitex, Inc., Alpharetta, GA (US); The Provost Fellows and Scholars of the College of the Holy and Undivided Trinity of Queen Elizabeth Near Dublin, Dublin (IE); The Texas A&M University System, College Station, TX (US)"

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,438 B1 | Page 1 of 1 |
| APPLICATION NO. | : 10/795267 | |
| DATED | : February 23, 2010 | |
| INVENTOR(S) | : Joseph M. Patti et al. | |

It is certified that error appears in the above-identified patent and that said Letters Patent is hereby corrected as shown below:

Title page (*) Notice

Delete "by 297 days" – and insert --by 743 days--

Signed and Sealed this

Twenty-fourth Day of August, 2010

David J. Kappos
*Director of the United States Patent and Trademark Office*